United States Patent
Simberg et al.

(10) Patent No.: US 9,730,637 B2
(45) Date of Patent: Aug. 15, 2017

(54) LAYERED PARTICLES FOR RETRIEVING DNA RELEASED FROM CELLS FROM A GASTROINTESTINAL TRACT SAMPLE AND METHODS FOR MAKING AND USING THEM

(75) Inventors: Dmitri Simberg, San Diego, CA (US); Yu-Tsueng Liu, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 50 days.

(21) Appl. No.: 14/238,189

(22) PCT Filed: Aug. 17, 2012

(86) PCT No.: PCT/US2012/051433
§ 371 (c)(1),
(2), (4) Date: May 16, 2014

(87) PCT Pub. No.: WO2013/028548
PCT Pub. Date: Feb. 28, 2013

(65) Prior Publication Data
US 2014/0288398 A1 Sep. 25, 2014

Related U.S. Application Data

(60) Provisional application No. 61/525,560, filed on Aug. 19, 2011.

(51) Int. Cl.
*G01N 21/75* (2006.01)
*B01D 35/00* (2006.01)
(Continued)

(52) U.S. Cl.
CPC .......... *A61B 5/6861* (2013.01); *A61B 5/1473* (2013.01); *A61B 5/14546* (2013.01);
(Continued)

(58) Field of Classification Search
None
See application file for complete search history.

(56) References Cited

U.S. PATENT DOCUMENTS 7,285,835 B2 * 10/2007 Rizzo ...................... H01L 43/08
257/295
7,699,979 B2 * 4/2010 Li .......................... B82Y 15/00
210/138

(Continued)

FOREIGN PATENT DOCUMENTS

WO    2010078569 A2    7/2010

OTHER PUBLICATIONS

Chang, Bong Ho, International Search Report and Written Opinion, PCT/US2012/051433, Korean Intellectual Property Office, Feb. 25, 2013.
(Continued)

*Primary Examiner* — Bradley L Sisson
(74) *Attorney, Agent, or Firm* — Greer, Burns & Crain, Ltd.; Gregory P. Einhorn

(57) ABSTRACT

In alternative embodiments, the invention provides compositions such as devices, pills, beads, capsules, products of manufacture, particles, microparticles, nanoparticles, gels, liquid gels, liquid gel capsules, capsules, tablets, geltabs, liquids, sprays, emulsions, suspensions, pastes or yogurts, for the detection and isolation of biomarkers, nucleic acids, proteins or peptides, proteoglycans, lipids, fats, sugars or polysaccharides in the gastrointestinal tract for e.g., detecting the presence of particular exogenous or endogenous nucleic acids, e.g., DNA or RNA, or proteins, in the gastrointestinal tract, for example, to diagnose the presence of an infectious or exogenous agent such as a virus, a fungus, a parasite, a bacteria, intestinal helminths and protozoan parasites, and the like, or a biomarker such as a cancer-causing or cancer-predisposing allele, e.g., mutations of the
(Continued)

KRAS2 oncogene in pancreatic cancer. In alternative embodiments, compositions of the invention comprise magnetic particles such as a magnetically-responsive microparticle or nanoparticle; a superparamagnetic bead or polystyrene bead; a superparamagnetic fine particle; a ferrimagnetic particle; or, a magnetic microsphere, nanosphere, microbead or nanobeads. In alternative embodiments, the invention provides methods for detecting, retrieving, capturing or isolating a sample of a nucleic acid, or an anionic, cationic or hydrophobic protein or peptide, a mucin, a phosphoprotein, a proteoglycan or a polysaccharide, in vivo.

19 Claims, 7 Drawing Sheets

(51) Int. Cl.
| | | |
|---|---|---|
| C12M 1/00 | (2006.01) | |
| A61B 5/00 | (2006.01) | |
| C12Q 1/68 | (2006.01) | |
| A61B 5/145 | (2006.01) | |
| A61B 5/1473 | (2006.01) | |
| A61B 10/00 | (2006.01) | |

(52) U.S. Cl.
CPC ........ *A61B 5/4848* (2013.01); *A61B 10/0045* (2013.01); *C12Q 1/6806* (2013.01); *A61B 2010/0061* (2013.01)

(56) References Cited

U.S. PATENT DOCUMENTS

| | | | |
|---|---|---|---|
| 7,771,707 B2 * | 8/2010 | Hirsh | A61K 9/145 424/10.1 |
| 7,781,027 B2 * | 8/2010 | Brown | B01L 3/00 427/487 |
| 2005/0112655 A1 | 5/2005 | Banerjee et al. | |
| 2008/0305101 A1 | 12/2008 | Ruoslahti et al. | |
| 2010/0254914 A1 | 10/2010 | Park et al. | |
| 2011/0202142 A1 * | 8/2011 | Mao et al. | 623/23.72 |
| 2014/0288398 A1 * | 9/2014 | Simberg | C12Q 1/6806 600/309 |

OTHER PUBLICATIONS

Longo et al., "Core-Shell Hydrogel Particles Harvest, Concentrate and Preserve Labile Low Abundance Biomarkers", PLos One, Mar. 10, 2009, vol. 4, No. 3, pp. 1-14.

Wittmann-Regis, Agnes, International Preliminary Report on Patentability, PCT/US2012/051433, The International Bureau of WIPO, Mar. 6, 2014.

* cited by examiner

SEQUENCE LISTING

```
<160> NUMBER OF SEQ ID NOS: 3

<210> SEQ ID NO 1
<211> LENGTH: 10
<212> TYPE: PRT
<213> ORGANISM: artificial sequence
<220> FEATURE:
<223> OTHER INFORMATION: synthetic peptide

<400> SEQUENCE: 1

Val Asn Val Asp Glu Val Gly Gly Glu Ala
1               5                   10

<210> SEQ ID NO 2
<211> LENGTH: 11
<212> TYPE: PRT
<213> ORGANISM: artificial sequence
<220> FEATURE:
<223> OTHER INFORMATION: synthetic peptide

<400> SEQUENCE: 2

Ser Thr Pro Asp Ala Val Met Gly Asn Pro Lys
1               5                   10

<210> SEQ ID NO 3
<211> LENGTH: 6
<212> TYPE: PRT
<213> ORGANISM: artificial sequence
<220> FEATURE:
<223> OTHER INFORMATION: synthetic peptide

<400> SEQUENCE: 3

Leu Thr Pro Glu Glu Lys
1               5
```

LAYERED PARTICLES FOR RETRIEVING DNA RELEASED FROM CELLS FROM A GASTROINTESTINAL TRACT SAMPLE AND METHODS FOR MAKING AND USING THEM

RELATED APPLICATIONS

This application is a national phase application claiming benefit of priority under 35 U.S.C.§371 to Patent Convention Treaty (PCT) International Application Serial No: PCT/US2012/051433, filed Aug. 17, 2012, which claims the benefit of priority under 35 U.S.C. §119(e) of U.S. Provisional Application No. 61/525,560, filed Aug. 19, 2011. The aforementioned applications are expressly incorporated herein by reference in their entirety and for all purposes.

GOVERNMENT RIGHTS

This invention was made with government support under grant numbers 1R21CA137721-01, and CA164880, awarded by the National Institutes of Health (NIH). The government has certain rights in the invention.

TECHNICAL FIELD

This invention generally relates to medical diagnostics and devices and gastroenterology. In particular, in alternative embodiments, the invention provides compositions such as devices, pills, beads, capsules, products of manufacture, particles, microparticles, nanoparticles, gels, liquid gels, liquid gel capsules, capsules, tablets, geltabs, liquids, sprays, emulsions, suspensions, pastes, or yogurts, for the detection and isolation of biomarkers, nucleic acids, proteins or peptides, proteoglycans, lipids, fats, sugars or polysaccharides in the gastrointestinal tract for e.g., detecting the presence of particular exogenous or endogenous nucleic acids, e.g., DNA or RNA, or proteins, in the gastrointestinal tract, for example, to diagnose the presence of an infectious or exogenous agent such as a virus, a fungus, a parasite, a bacteria, intestinal helminths and protozoan parasites, and the like, or a biomarker such as a cancer-causing or cancer-predisposing allele, e.g., mutations of the KRAS2 oncogene in pancreatic cancer. In alternative embodiments, compositions of the invention comprise magnetic particles such as a magnetically-responsive microparticle or nanoparticle; a superparamagnetic bead or polystyrene bead; a superparamagnetic fine particle; a ferrimagnetic particle; or, a magnetic microsphere, nanosphere, microbead or nanobeads. In alternative embodiments, the invention provides methods for detecting, retrieving, capturing or isolating a sample of a nucleic acid, or an anionic, cationic or hydrophobic protein or peptide, a mucin, a phosphoprotein, a proteoglycan or a polysaccharide, in vivo.

BACKGROUND

Cancers of digestive system account for greater than 18% of cancers; out of 274,000 diagnosed, greater than 130,000 die per year. 43,140 men and women were diagnosed with and 36,800 died of cancer of the pancreas in 2010.

Pancreatic cancer is often a fatal disease with 5-year survival rates of only 1% to 4%. Early detection can substantially reduce the mortality rate. Simple, non-invasive screening tests are urgently needed to improve the current low survival rate of cancer patients.

There are several high-risk factors for pancreatic cancer, including family history, smoking, diabetes and obesity. These groups are primary candidates for pancreatic cancer screening. Mutations of the KRAS2 (also known as v-Ki-ras2 Kirsten rat sarcoma 2 viral oncogene homolog) oncogene (such as in codon 12) are present in approximately 90% to 95% of cases of pancreatic cancer. Despite the fact that KRAS mutations are not entirely specific to pancreatic cancer, the early detection of these mutations in high-risk individuals can save lives.

At the early stages of the cancer disease, cancerous cells and DNA are shed into the duodenum along with the pancreatic secretions. In the same fashion, biomarkers from stomach, esophagus, gall bladder and liver are shed into the GI tract. Serum biomarkers such as circulating tumor cells and circulating DNA appear relatively later in the disease.

Pancreatic secretions can be obtained endoscopically, but the procedure causes significant discomfort and cannot be used for routine screening. Stool is another source of gastrointestinal cancer-derived DNA that can be used for early screening. However, the sensitivity of detection of pancreatic cancer in stool is relatively low. The hostile environment of the gastrointestinal tract composed of bile salts, DNases, and bacteria reduces the chances that pancreatic cancer-derived DNA will survive during the passage.

Current early diagnostic methods of cancer include: endoscopic ultrasound, which are sensitive, but expensive and not for screening, and endoscopy is invasive; imaging (CT, MRI), which are expensive and cannot be used screening; and, blood testing for carbohydrate antigen 19-9, also called cancer antigen 19-9, or CA19-9, which gives a large proportion of false negatives and false positives.

For stomach and esophageal cancers, no screening procedure is available besides endoscopy. However, this is a costly procedure and is usually performed only in high risk populations such as in Japan.

SUMMARY

In alternative embodiments, the invention provides compositions, devices, pills, beads, capsules, products of manufacture, particles, microparticles or nanoparticles comprising:

(a) an outer shell or layer and an inner core or layer, wherein the outer shell or layer comprises an outer surface that is at least partially hydrophilic, or is substantially hydrophilic, or is hydrophilic, and is substantially or completely neutral in charge, and the outer shell or layer, or the outer shell or layer and the inner core or layer, comprises a hydrogel having:

(i) pores having sizes of (or an average pore size of) at least about, or about: 1 nm, 1.5 nm, 2 nm, 2.5 nm, 3 nm, 3.5 nm, 4 nm, 5 nm, 10 nm, 15 nm, 20 nm, 25 nm, 30 nm, 40 nm, 50 nm, 60 nm, 70 nm, 80 nm, or 90 nm or more; or, between about 1 nm and about 100 nm, and optionally the pores are no more than 100 nm in size; or pores having an about 9, 10 or 11 kilodalton (kDa) molecular weight cutoff (molecules, micelles, viruses, bacteria and the like greater than this size (about 9, 10 or 11 kDa) will not pass through the hydrogel pores); or (ii) a non-porous nature having molecular weight at least about 2 kDa, and optionally the hydrogel comprises a polyethylene glycol (PEG) or a quaternized polyethylenimine (PEI);

and the inner core or layer comprises a positively charged (cationic), anionic, or mixed cationic-anionic, or hydrophobic, or mixed cationic-anionic-hydrophobic composition, polymer, molecule or particle;

and optionally the inner core or layer has a high charge (positive or negative) density of at least about 10, 20, 30, 40 or 50 or more charges per 3 kDa molecular weight, and optionally quaternary, tertiary, primary or secondary amines, or combination thereof, or guanidine, a quaternized polyethylenimine (PEI), a pentamethylguanidine, heptamethylisobiguanide or Hunig's base or mixture thereof, contribute all or part of the charge, and optionally when the inner core or layer inner is partially, substantially or completely a hydrophobic core or layer, the inner core or layer inner comprises hydrophobic polymers or amino acid residues, optionally comprising phenylalanine, tryptophan and/or tyrosine;

(b) the device, pill, bead, capsule, product of manufacture, particle, microparticle or nanoparticle of (a), wherein the inner core or layer optionally comprises a hydrogel, and the hydrogel of the outer shell or layer, and the inner core or layer if present, comprises:

(i) a dextran, a cellulose, a methylcellulose, a sodium carboxymethylcellulose, an ethylcellulose, a hydroxymethyl cellulose, a microcrystalline cellulose, a dextrin, an alginate or alginic acid, a carrageenan, a gellan or a gelatin, a hyaluronan, a pullulan, a xanthan, a chitosan, a maltodextrin, a xyloglycan, a pectin, a quaternized polyethylenimine (PEI), or a polyethylene glycol (PEG), or (ii) a cross-linked and/or branched dextran, cellulose, methylcellulose, sodium carboxymethylcellulose, ethylcellulose, hydroxymethyl cellulose, microcrystalline cellulose, dextrin, alginate or alginic acid, carrageenan, gelian or gelatin, hyaluronan, pullulan, xanthan, chitosan, maltodextrin, xyloglycan, pectin, or polyethylene glycol (PEG), wherein optionally a branched or crosslinked hydrogel is prepared by thermal crosslinking, UV crosslinking, irradiation crosslinking, radical crosslinking or chemical crosslinking; or (iii) a mixed hydrogel or mixed polysaccharide/polymer hydrogel, or a cellulose/polyethyleneimine, cellulose/methacrylate, or (iv) a lyophilized, dry or dessicated hydrogel, wherein optionally the lyophilized, dry or dessicated hydrogel expands up to 500 times its lyophilized, dry or dessicated volume after contact with an aqueous environment, and optionally the lyophilized, dry or dessicated hydrogel substantially expands within 30 minutes;

(c) the device, pill, bead, capsule, product of manufacture, particle, microparticle or nanoparticle of (a) or (b), wherein the outer shell or layer and/or an inner core or layer comprises a plurality of magnetic molecules or particles, wherein optionally:

the outer shell or layer comprises a plurality of magnetic molecules or particles, or the inner core or layer comprises a plurality of magnetic molecules or particles, or both the outer shell or layer and the inner core or layer comprise a plurality of magnetic molecules or particles, or the magnetic particles are coated with a hydrophilic, a charged, a negatively charged, a positively charged (cationic), anionic, or a mixed cationic-anionic, or hydrophobic, or mixed cationic-anionic-hydrophobic polymer or a densely (positively or negatively) charged polymer, and;

(d) the device, pill, bead, capsule, product of manufacture, particle, microparticle or nanoparticle of (a), (b) or (c), wherein the positively charged (cationic), anionic, or mixed cationic-anionic, or hydrophobic, or mixed cationic-anionic-hydrophobic composition, molecule or particle of the inner core or layer comprises a nanoparticle, microparticle or polymer that is positively charged (cationic), anionic, or mixed cationic-anionic, or hydrophobic, or mixed cationic-anionic-hydrophobic, wherein optionally the composition, molecule or particle of the inner core or layer is microencapsulated;

(e) the device, pill, bead, capsule, product of manufacture, particle, microparticle or nanoparticle of any of (a) to (d), wherein the hydrogel comprises an expandable hydrogel, a rapidly expandable hydrogel, a magnetic hydrogel or a rapidly expandable magnetic hydrogel;

(f) the device, pill, bead, capsule, product of manufacture, particle, microparticle or nanoparticle of any of (a) to (e), wherein the device, pill, bead, capsule, product of manufacture, particle, microparticle or nanoparticle:

(i) is formulated for ingestion for a human or an animal,
  (ii) is encapsulated in an enteric coating,
  (iii) comprises a coating resistant in the gastric pH but removable in duodenal pH, or dissolves or disintegrates in duodenal pH,
  (iv) is encapsulated in a capsule, tablet or geltab or the like that partially or completely dissolves or disintegrates in duodenal pH, or at a pH of between about 5 and 6, or at a pH more alkaline than a pH of about 5;

(g) the device, pill, bead, capsule, product of manufacture, particle, microparticle or nanoparticle of any of (a) to (f), wherein the device, pill, bead, capsule, product of manufacture, particle, microparticle or nanoparticle further comprises a "control" nucleic acid or protein or peptide, wherein optionally the type and/or amount of nucleic acid, protein or peptide is known;

(h) the device, pill, bead, capsule, product of manufacture, particle, microparticle or nanoparticle of any of (a) to (g), wherein the plurality of magnetic molecules or particles comprises a magnetically-responsive microparticle or nanoparticle; a superparamagnetic bead or polystyrene bead; a superparamagnetic fine particle; a ferrimagnetic particle; or, a magnetic microsphere, nanosphere, microbead or nanobeads;

(i) the device, pill, bead, capsule, product of manufacture, particle, microparticle or nanoparticle of any of (a) to (h), wherein the device, pill, bead, capsule, product of manufacture, particle, microparticle or nanoparticle is bilayered or multilayered; or (j) the device, pill, bead, capsule, product of manufacture, particle, microparticle or nanoparticle of any of (a) to (i), wherein the device, pill, bead, capsule, product of manufacture, particle, microparticle or nanoparticle captures a biomarker in vivo in the presence of bile acids, proteases and/or DNases within range of pH from 2.0 to 9.0, or captures biomarkers in presence of bile acid concentrations from about 0.1 mg/ml to 50 mg/ml, or captures biomarkers in presence of DNase from between about 0.1 to 20 mg/ml.

In alternative embodiments, the invention provides gels, liquid gels, liquid gel capsules, capsules, tablets or geltabs for administration, e.g., oral administration, comprising:

(a) a device, pill, bead, capsule, product of manufacture, particle, microparticle or nanoparticle of the invention, or (b) a device, pill, bead, capsule, product of manufacture, particle, microparticle or nanoparticle of the invention, and further comprising: a protein or peptide, a polysaccharide, a sugar, a fat, a lipid, a secretin, a DNase inhibitor, an EGTA, an EDTA, an actin, a polycations, a flavoring agent or a coloring agent, or a mixture thereof or a combination thereof;

wherein the gel, liquid gel, liquid gel capsule, capsule, tablet or geltab comprises (or is encapsulated by):
(i) an enteric coating that partially or completely dissolves or disintegrates in duodenal pH,
(ii) a coating, or enteric coating, resistant to gastric pH but removable in duodenal pH, or dissolves or disintegrates in duodenal pH, or
(iii) a coating, or enteric coating, that partially or completely dissolves or disintegrates in duodenal pH, or at a pH of between about 5 and 6, or at a pH more alkaline than a pH of about 5;
wherein optionally the device, pill, bead, capsule, product of manufacture, particle, microparticle or nanoparticle captures a biomarker in vivo in the presence of bile acids, proteases and/or DNases within range of pH from 2.0 to 9.0, or captures biomarkers in presence of bile acid concentrations from about 0.1 mg/ml to 50 mg/ml, or captures biomarkers in presence of DNase from between about 0.1 to 20 mg/ml.

In alternative embodiments, the invention provides methods for detecting, retrieving, capturing or isolating a sample of a nucleic acid, or an anionic, cationic or hydrophobic protein or peptide, a mucin, a phosphoprotein, a proteoglycan or a polysaccharide, in vivo comprising:
(a)
(i) providing a device, pill, bead, capsule, product of manufacture, particle, microparticle or nanoparticle of the invention, or a gel, liquid gel, liquid gel capsule, capsule, tablet or geltab of the invention,
wherein optionally the device, pill, bead, capsule, product of manufacture, particle, microparticle or nanoparticle captures a biomarker in vivo in the presence of bile acids, proteases and/or DNases within range of pH from 2.0 to 9.0, or captures biomarkers in presence of bile concentrations from 1 mg/ml to 50 mg/ml, or captures biomarkers in presence of DNase from between about 0.1 to 20 mg/ml or protease from between about 0.1 and 20 mg/ml;
(ii) orally administering the device, pill, bead, capsule, product of manufacture, particle, microparticle or nanoparticle, or tablet, geltab or capsule, to an individual, or delivering the device, pill, bead, capsule, product of manufacture, particle, microparticle or nanoparticle, or tablet, geltab or capsule, into the mouth, stomach, gut, intestine or gastrointestinal tract of an individual, and
(iii) harvesting or recovering the device, pill, bead, capsule, product of manufacture, particle, microparticle or nanoparticle from the individual;
(b) the method of (a), wherein the individual is a human or an animal;
(c) the method of (a) or (b), wherein the device, pill, bead, capsule, product of manufacture, particle, microparticle or nanoparticle is recovered from a stool, a lavage or a biopsy;
(d) the method of any of (a) to (c), wherein the device, pill, bead, capsule, product of manufacture, particle, microparticle or nanoparticle is recovered or harvested from the individual from a passed stool or feces, using or by means of:

(i) a magnetic source, wherein optionally the magnetic source is a magnetic bead or column, or
(ii) a color marker;
(e) the method of any of (a) to (c), wherein the device, pill, bead, capsule, product of manufacture, particle, microparticle or nanoparticle is recovered or harvested from the individual using an endoscope, or
(f) the method of any of (a) to (e), wherein two or more or several, or a plurality of, devices, pills, beads, capsules, products of manufacture, particles, microparticles or nanoparticles, or gels, liquid gels, liquid gel capsules, capsules, tablets or geltabs, are administered at the same time, or about the same time, or on the same day.

In alternative embodiments the methods further comprise:
(a) detecting, analyzing, sequencing and/or quantifying the nucleic acid or protein or peptide, mucin, phosphoprotein, proteoglycan or polysaccharide associated with the device, pill, bead, capsule, product of manufacture, particle, microparticle or nanoparticle,
wherein optionally the nucleic acid or protein or peptide, mucin, phosphoprotein, proteoglycan or polysaccharide is electrostatically bound (or bound via its charge) to the charged (e.g., positively or negatively charged) composition, molecule or particle, and the nucleic acid or protein or peptide, or proteoglycan or polysaccharide, is released from the device, pill, bead, capsule, product of manufacture, particle, microparticle or nanoparticle after its recovery or harvesting;
(b) co-administration of a DNase inhibitor, wherein optionally the DNase inhibitor is an EGTA, an EDTA, an actin, a polycation or a mixture thereof, wherein optionally the DNase inhibitor is contained within the device, pill, bead, capsule, product of manufacture, particle, microparticle or nanoparticle of the invention, or the gel, liquid gel, liquid gel capsule, capsule, tablet or geltab of the invention; or
(c) co-administration of a protein or peptide, a polysaccharide, a sugar, a fat, a lipid, a secretin, a DNase inhibitor, an EGTA, an EDTA, an actin, a polycations, a flavoring agent or a coloring agent, or a mixture thereof or a combination thereof wherein optionally the protein or peptide, polysaccharide, sugar, fat or lipid, secretin, DNase inhibitor, EGTA, EDTA, actin, polycation, flavoring agent or coloring agent is contained within the device, pill, bead, capsule, product of manufacture, particle, microparticle or nanoparticle of the invention, or the gel, liquid gel, liquid gel capsule, capsule, tablet or geltab of the invention.

In alternative embodiments the methods further comprise: testing for or detecting or measuring the presence of, or the amount of:
(a) a DNA, genomic DNA, RNA, microRNA or miRNA, wherein the nucleic acid is a DNA, a genomic DNA, an RNA, a microRNA or a miRNA;
(b) the method of (a), wherein the nucleic acid or protein or peptide, lipid, proteoglycan, sugar, polysaccharide, lipid or fat is derived from a tumor cell, a cancer cell, a dysfunctional cell or an exogenous cell,
wherein optionally the exogenous cell is a virus, a fungus, a parasite, a bacteria, an intestinal helminth or a protozoan parasite and the like, or occult blood and/or its components shed from any part of GI tract,
wherein optionally the protein or peptide is derived from a hemoglobin or other erythrocyte protein, a human hemoglobin or other human erythrocyte protein, or the protein or peptide is generated after hemoglobin or protein cleavage;

(c) a biomarker, wherein optionally the biomarker comprises a nucleic acid, a polypeptide or a peptide, a proteoglycan, a lipid, a fat, a sugar or a polysaccharide;

(d) the method of (c), wherein the nucleic acid or protein or peptide, proteoglycan, lipid, fat, sugar or polysaccharide, is or comprises a biomarker for a disease or an infection, or is a biomarker for a predisposition to a disease or infection, and optionally the biomarker is or comprises a peptide or protein mutation or truncation, a methylation, a chemical modification to a protein or peptide, a methylation, a citrullination, an acetylation, a phosphorylation, a SUMOylation, a ubiquitination, an ADP-ribosylation or a histone modification.

and optionally the biomarker is or comprises a DNA, a genomic DNA, an RNA, a non-coding RNA, a microRNA or a miRNA, a nucleic acid structure alteration, a chromosome translocation, a telomere shortening, a deletion, an inversion, an amplification, a fusion mRNA transcript, or an alternative splicing, and optionally the biomarker is or comprises a proteoglycan, lipid, fat, sugar or polysaccharide; or (e) wherein the nucleic acid comprises an oncogene mutation, and optionally the oncogene comprises or is a BRAF, CDH1, BRCA-1, BRCA-2, p53 or KRAS2 oncogene; or the nucleic acid has a gene methylation, and optionally the gene methylation comprises a p16 or a ppENK, and/or the nucleic acid is a biomarker for a cancer, or a pancreatic, gastric, esophageal, gall bladder liver and/or colon cancer.

In alternative embodiments the methods comprise diagnosing, predicting (e.g., assessing the predisposition for acquiring), or making a prognosis of a disease, condition or infection by detecting, analyzing, sequencing and/or quantifying the biomarker, nucleic acid or protein or peptide, proteoglycan, lipid, fat, sugar or polysaccharide associated with the device, pill, bead, capsule, product of manufacture, particle, microparticle or nanoparticle, wherein the biomarker, nucleic acid or protein or peptide, proteoglycan, lipid, fat, sugar or polysaccharide is a biomarker for the disease, condition or infection.

In alternative embodiments the methods comprise assessing the effectiveness of a treatment or a medication for a disease, condition or infection by detecting, analyzing, sequencing and/or quantifying the biomarker, nucleic acid or protein or peptide, proteoglycan, lipid, fat, sugar or polysaccharide associated with ("captured by") the device, pill, bead, capsule, product of manufacture, particle, microparticle or nanoparticle, wherein the biomarker, nucleic acid or protein or peptide, proteoglycan, lipid, fat, sugar or polysaccharide is a biomarker for the disease, condition or infection.

In alternative embodiments the methods comprise assessing, detecting, quantifying or measuring the amount or location of:

a peptide or protein mutation or truncation, a methylation, a chemical modification to a protein or peptide, a methylation, a citrullination, an acetylation, a phosphorylation, a SUMOylation, a ubiquitination, an ADP-ribosylation or a histone modification.

a DNA, a genomic DNA, an RNA, a non-coding RNA, a microRNA or a miRNA, a nucleic acid structure alteration, a chromosome translocation, a telomere shortening, a deletion, an inversion, an amplification, a fusion mRNA transcript, or an alternative splicing; or an oncogene mutation, or an oncogene comprising a BRAF, CDH1, BRCA-1, BRCA-2, p53 or KRAS2 oncogene, or a gene methylation, or a gene methylation comprising a p16 or a ppENK, or a biomarker for a cancer, or a pancreatic, gastric, esophageal, gall bladder liver and/or colon cancer.

In alternative embodiments the invention provides kits comprising:

(a) a device, pill, bead, capsule, product of manufacture, particle, microparticle or nanoparticle of the invention, or the gel, liquid gel, liquid gel capsule, capsule, tablet or geltab of the invention;

(b) the kit of (a), further comprising instructions to practice a method of the invention, or further comprising instructions to a patient user, which optionally includes instructions to place the sample in a preservative solution, and/or to return the harvested or recovered device, pill, bead, capsule, product of manufacture, particle, microparticle or nanoparticle of the invention, or the gel, liquid gel, liquid gel capsule, capsule, tablet or geltab of the invention, to a lab for analysis; or (c) the kit of (a) or (b), further comprising a vial for storage of the device, pill, bead, capsule, product of manufacture, particle, microparticle or nanoparticle after recovery from the stool or feces, and optionally the kit further comprises a preservative solution for stabilizing and/or preventing the hydrolysis or breakdown of nucleic acid or protein or peptide in the recovered or harvested device, pill, bead, capsule, product of manufacture, particle, microparticle or nanoparticle.

In alternative embodiments the invention provides liquids, sprays, emulsions, suspensions, pastes, yogurts, gels, tablets or geltabs formulated for oral administration comprising a device, pill, bead, capsule, product of manufacture, particle, microparticle or nanoparticle of the invention or a gel, liquid gel, liquid gel capsule, capsule, tablet or geltab of the invention.

In alternative embodiments the invention provides methods for elution and further purification of nucleic acid, protein or peptide, proteoglycan, lipid, fat, sugar or polysaccharide detected, retrieved, captured or isolated using: a device, pill, bead, capsule, product of manufacture, particle, microparticle or nanoparticle of the invention; a gel, liquid gel, liquid gel capsule, capsule, tablet or geltab of the invention; a liquid, a spray, an emulsion, a suspension, a paste, a yogurt, a gel, a tablet or a geltab of the invention; a kit of the invention; or, using a method of any of the invention; or, using a method of any the invention, comprising:

(a) recovering all or part of a sample, or a stool or feces sample, from a device, pill, bead, capsule, product of manufacture, particle, microparticle or nanoparticle of the invention; a gel, liquid gel, liquid gel capsule, capsule, tablet or geltab of the invention; a liquid, a spray, an emulsion, a suspension, a paste, a yogurt, a gel, a tablet or a geltab of the invention; a kit of the invention; or, using a method of any of the invention, after it has passed through all or part of the GI tract, and placing or applying all or part of the sample on a bead, a resin, a column, a filter, a membrane, or a filter membrane;

(b) washing the sample that has been placed or applied to the bead, resin, column, filter, membrane or filter membrane, wherein optionally the wash comprises use of a buffer and/or a vacuum;

(c) eluting molecules attached to the bead, resin, column, filter, membrane or filter membrane with a combination of a vacuum and: a salt elution buffer, a pH elution buffer, a reducing agent, or any other elution composition or buffer, and/or cleaving all or part of the sample from the bead, resin, column, filter, membrane or filter membrane, and optionally a molecule of interest from the eluted sample is further trapped or isolated in a trapping compartment or device, which optionally can be on a low molecular weight (MW) cutoff filter, bead, resin or membrane, optionally having a cutoff of not less than about 1 kDa, 3 kDa, 10 kDa, 30 kDa 50 kDa or 100 kDa, or on a membrane, resin or column, or optionally is trapped or isolated in a second container.

and optionally an analysis reaction is performed, which optionally can be performed directly in a trapping compartment or container, which optionally is or comprises a PCR device or PCR tube, an ELISA well or a blotting paper, and optionally the device, pill, bead, capsule, product of manufacture, particle, microparticle or nanoparticle after recovery from the stool or feces is placed and processed automatically, and optionally the trapping compartment with the nucleic acid or protein or peptide, proteoglycan, lipid, fat, sugar or polysaccharide recovered after elution from device, pill, bead, capsule, product of manufacture, particle, microparticle or nanoparticle after recovery from the stool or feces is applied to a downstream processing or analytical equipment or device, which optionally comprises a PCR, an ELISA, an immunoblotting, an array or a microarray, a quantitative PCR, a cell assay, a high performance liquid chromatography (HPLC), a chromatography, an electrophoresis, a filtration and/or an ultrafiltration, and the like.

In alternative embodiments the invention provides devices for practicing the method of the invention, comprising the components used to practice a method of the invention, wherein the device, pill, bead, capsule, product of manufacture, particle, microparticle or nanoparticle after recovery from the stool or feces is placed and processed automatically.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

BRIEF DESCRIPTION OF THE DRAWINGS

The drawings set forth herein are illustrative of embodiments of the invention and are not meant to limit the scope of the invention as encompassed by the claims.

Figures are described in detail herein.

FIG. 1 and FIG. 2 are schematic representations of the effect of administered particles of the invention on the pancreatic cancer DNA in the GI tract.

FIG. 5 illustrates images of DNA stained with SyBr Gold. Bile and DNase decreased the amount of absorbed DNA, but did not completely remove it;

FIG. 6 illustrates DNA analyzed on agarose gel stained with CyBr Green, as described in Example 2, below.

Like reference symbols in the various drawings indicate like elements.

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

In alternative embodiments, the invention provides a device, capsule, product of manufacture, particle or nanoparticle comprising a hydrogel, e.g., a rapidly expandable magnetic hydrogel, with a charged core. Compositions of the invention (e.g., capsule), when ingested by a human or animal, will sample (absorb) the pancreatic juice and the bile in duodenum. The juice or material absorbed or "captured" or "sampled" by a device, capsule, product of manufacture, particle or nanoparticle of the invention can comprise, for example, cellular nucleic acid, cancer cell nucleic acid, e.g., DNA or RNA, cancer protein and cancer cells, biomarkers, nucleic acids, proteins or peptides, proteoglycans, lipids, fats, sugars or polysaccharides.

The hydrophobic and/or charged (cationic or anionic) moieties, e.g., in a core or interior of a device, capsule, product of manufacture, particle or nanoparticle of the invention, will bind biomarkers, e.g., nucleic acids, e.g., DNA or RNA, proteins or peptides, proteoglycans, lipids, fats, sugars or polysaccharides, and will protect these molecules from DNase or protease or other enzyme degradation until the composition of the invention (e.g., capsule) is excreted in stool or otherwise harvested, e.g., by endoscope. The cationic moieties, e.g., in a core of a capsule, also can bind anionic proteins and other negatively charged molecules. Similarly, anionic moieties can bind cationic biomarkers and hydrophobic moieties can bind proteins and peptides and other positively charged molecules.

In alternative embodiments, an excreted or otherwise harvested composition of the invention, e.g., a device, pill, bead, capsule, product of manufacture, particle, microparticle or nanoparticle, can be easily recovered, e.g., via a magnetic source such as a column, or could be recognized due to a color property, or is harvested by endoscope. The nucleic acid (e.g., DNA or RNA), or protein or peptides, can then be analyzed and/or quantified by various analytical methods, e.g., molecular analysis techniques such as detecting and/or quantifying a nucleic acid biomarker, such as a KRAS mutation.

Figure 1A:
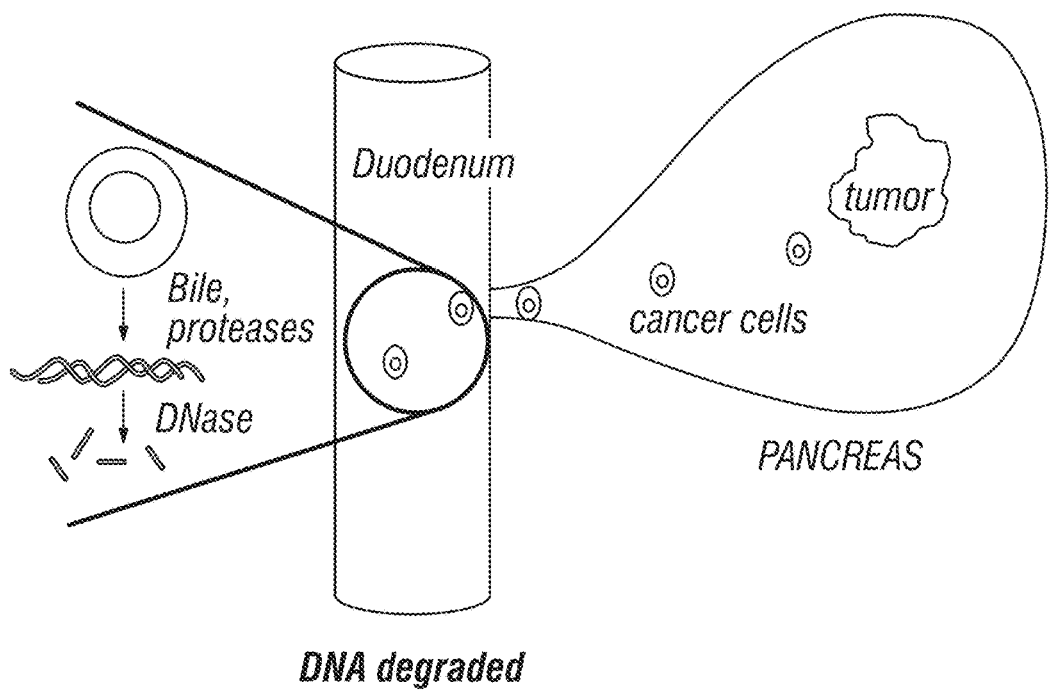
FIG. 1A: once secreted into the duodenum, nucleic acid, e.g., DNA, from cells, e.g., cancer cells, is subject to degradation.
Figure 1B:
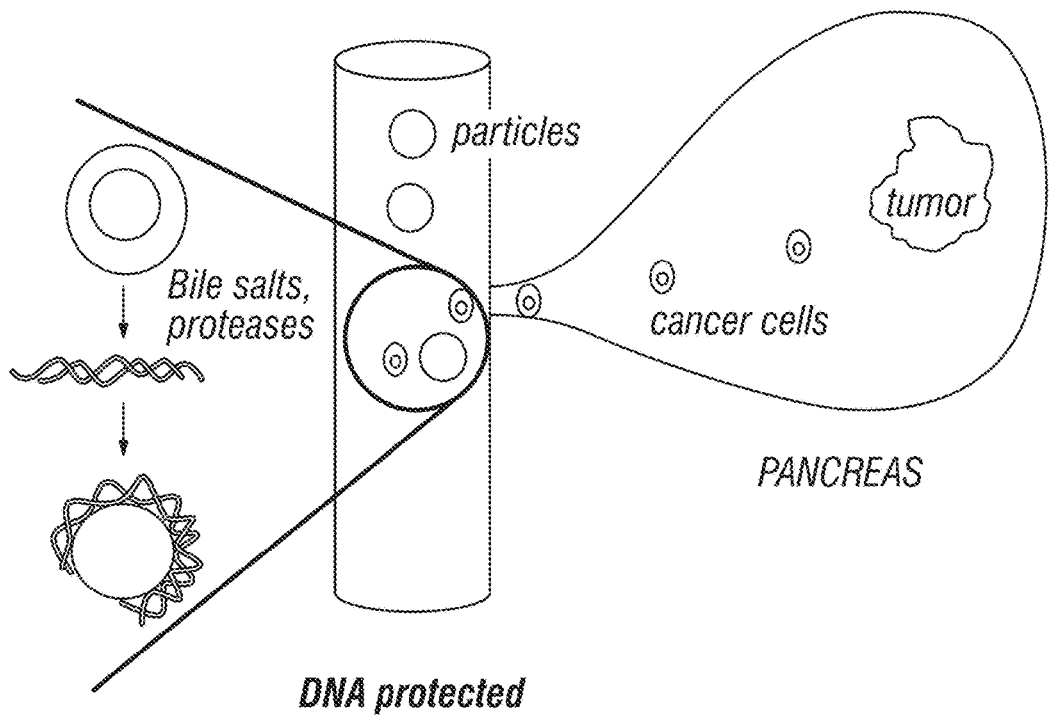
FIG. 1B: the DNA is protected by ingested particles.
Figure 2:
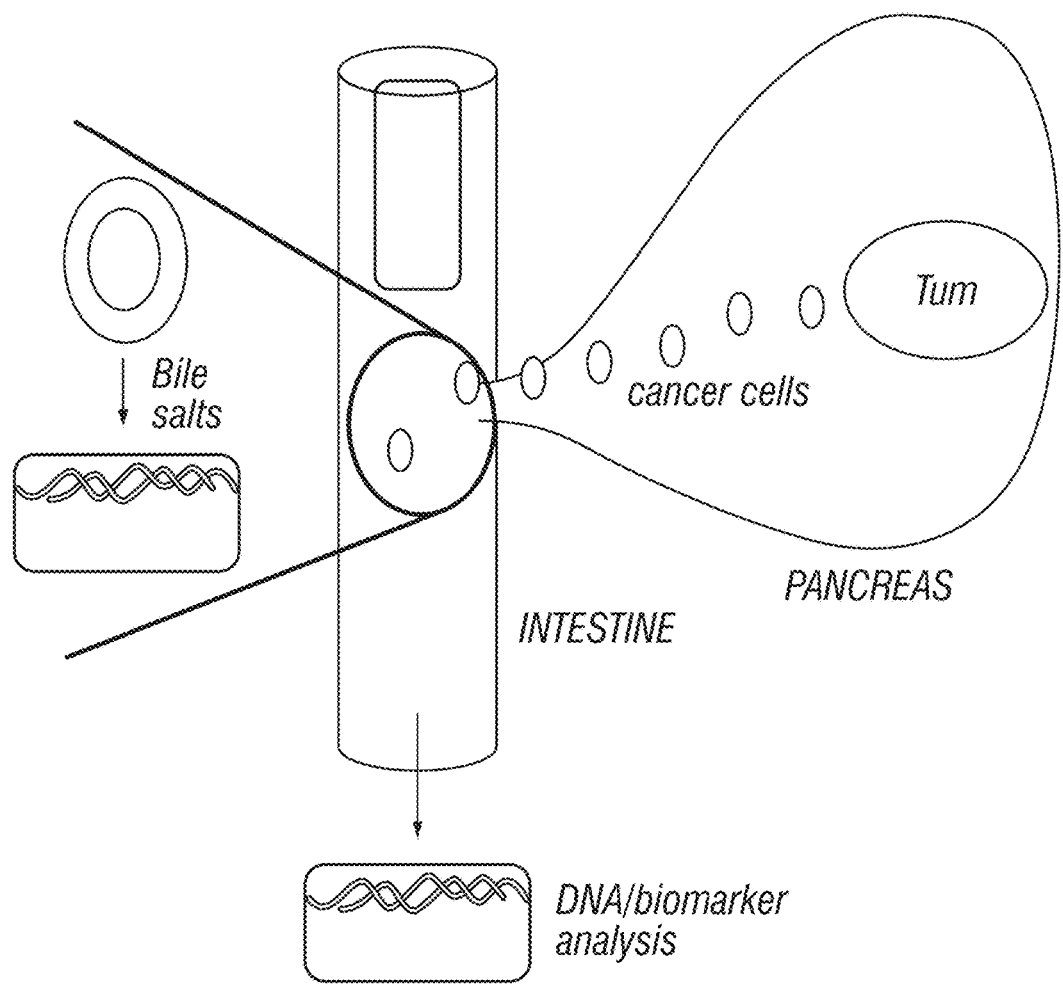

In alternative embodiments, the invention provides ingestible, charged, polymer-coated devices, capsules, products of manufacture, particles, microparticle or nanoparticles, which optionally comprise magnetic particles, that can bind and protect a nucleic acid, e.g., an exfoliated cancer nucleic acid, e.g., DNA or RNA, or a protein or a peptide, fat, lipid, sugar or polysaccharide and the like, in the presence of bile, proteases and pancreatic juice secretions, e.g., as illustrated in FIG. 1B and FIG. 2. In alternative embodiments, the ingestible, charged polymer-coated devices, capsules, products of manufacture, particles or nanoparticles of the invention are orally administered to harvest or capture a biomarker, e.g., a nucleic acid, in the lumen of the gut, e.g., an exfoliated nucleic acid, e.g., DNA or RNA, or other biomarkers, e.g., proteins or peptides, proteoglycans, lipids, fats, sugars or polysaccharides, and protect it from destruction, thereby improving the recovery of e.g., cancer nucleic acid, e.g., DNA or RNA, or protein or peptide, from e.g., a stool or feces. In one embodiment, the end result will be the increased sensitivity of detection and/or quantifying of a cancer biomarker, e.g., an oncogene such as a KRAS mutation, or proteins or peptides, proteoglycans, lipids, fats, sugars or polysaccharides in a stool or feces.

In alternative embodiment, the device can capture the products of degradation of hemoglobin, such as hydrophobic peptides VNVDEVGGEA (SEQ ID NO:1), STPDAVMGNPK (SEQ ID NO:2) and LTPEEK (SEQ ID NO:3) that are generated by pepsin, trypsin and chymotrypsin.

In alternative embodiments, the invention provides ingestible, charged, polymer-coated devices, capsules, products of manufacture, particles, microparticle or nanoparticles that capture and protect a nucleic acid, e.g., a cancer nucleic acid, e.g., DNA or RNA, protein, peptide, mucins, phosphoproteins, proteoglycans or polysaccharides in a duodenal environment in vitro and in vivo.

In alternative embodiments, the compositions of the invention comprise magnetic particles coated with densely charged polymer. The capture, protection and magnetic isolation of cancer nucleic acid, e.g., DNA or RNA, can be optimized depending on what tumor cells are being detected, e.g., whether pancreatic tumor cells are to be detected, and varying levels and environments of bile acids and pancreatic juice enzymes.

The efficiency of capture and protection of the biomarker, e.g., a nucleic acid, e.g., DNA or RNA protein, peptide, mucins, phosphoproteins, proteoglycans, proteoglycans or polysaccharides can be determined by gel electrophoresis and/or by PCR analysis or ELISA of the oncogene or biomarker to be detected, e.g., a KRAS G12D mutation.

The impact of use of compositions of the invention can have a high payoff for the public health, for example, use of compositions of the invention can result in the improved recovery and/or improved detection sensitivity of a biomarker in a feces or stool, e.g., a cancer biomarker, e.g., a KRAS2 mutation, to improve on the early detection of a cancer, e.g., a pancreatic cancer, in a predisposed population. In alternative embodiments, compositions of the invention are employed for recovery, detection, quantification and/or discovery of other biomarkers, e.g., cancer biomarkers, such as oncogenes, e.g., such as pancreatic cancer biomarkers, or other biomarkers such as gene methylation, telomere shortening, RNA and proteins for any disease, condition and/or infection.

In alternative embodiments, use of a non-invasive method of this invention for screening for early cancers, e.g., a pancreatic cancer, can add to early detection compliance in the population, as compared to the invasive endoscopy. Use of compositions of the invention can reduce the use of expensive imaging for early screening and reduce costs In alternative embodiments, compositions of the invention comprise magnetic particles, which can greatly facilitate the process of recovery of the composition, and its "payload", e.g., nucleic acid (e.g., DNA or RNA) or proteins or peptides, from stool, lavage or feces. In alternative embodiments, compositions of the invention are used for fecal screening and diagnostics for many types of gastrointestinal (GI) conditions, infections and/or cancers and malignancies. In alternative embodiments, compositions of the invention assist in early screening of a variety of (GI) conditions, infections and/or cancers and malignancies.

In alternative embodiment, the compositions of the invention comprise a purification method or device wherein the device, capsule, product of manufacture, particle or nanoparticle recovered from stools or feces, or sample from an endoscope, and then is directly applied on a filter, a membrane, or a filter membrane, washed and then bound molecules of interest are eluted using e.g., a elution buffer or a vacuum; and optionally the eluted molecules of interest are further trapped in an attachable compartment that is compatible with a downstream molecular analysis or protocol, such as e.g., a PCR apparatus or a PCR tube, an ELISA microwell, a microarray or a microfluidic chip.

In alternative embodiments, compositions of the invention are formulated for and used as orally administered particles for capture and protection of cancer biomarkers in the GI tract. In alternative embodiments, the cationic particles of compositions of the invention prolong sample storage and improve sample quality. Use of magnetic particles that are excreted in stool can greatly simplify the DNA extraction and recovery for molecular analysis.

Thus, this invention has a high impact on the diagnosis and monitoring of cancers, e.g., such as pancreatic cancers. The non-invasive sampling of cancer nucleic acid, e.g., DNA or RNA, can improve feasibility of early screening of pancreatic cancer in high-risk populations, and can be a cost effective screening and monitoring tool.

Products of Manufacture, Kits

The invention also provides products of manufacture, kits and pharmaceuticals for practicing the methods of this invention. In alternative embodiments, the invention provides products of manufacture, kits and/or pharmaceuticals comprising all the components needed to practice a method of the invention.

Hydrogels

In alternative embodiments, compositions of the invention comprise a hydrogel, which can be any macromolecular networks that contains a large fraction of solvent within their structure and do not dissolve, or, a colloidal gel in which water is the dispersion medium of the colloid having a mixture with properties between those of a solution and fine suspension (a colloid gel is a colloid in a more solid form than a sol). In alternative embodiments, compositions of the invention comprise a "non-responsive" hydrogel, e.g., a simple polymeric network that dramatically swells upon exposure to water, and/or a "responsive" hydrogel, e.g., a gel having added functionality and display changes in solvation in response to certain stimuli such as temperature. Any non-toxic hydrogel can be used.

For example, in alternative embodiments, compositions of the invention comprise a hydrogel comprising: an acacia, alginic acid, sodium carboxymethylcellulose, microcrystalline cellulose, dextrin, ethylcellulose, gelatin, liquid glucose, polyvinyl pyrrolidone, carboxyvinyl polymer, methylcellulose, hydroxymethyl cellulose, low molecular weight polyethylene oxide polymers, hydroxyethyl cellulose, hydroxypropyl cellulose, hydroxypropyl methylcellulose (HPMC), gums, acrylate polymers, methacrylate polymers and/or maltodextrin and/or mixtures thereof.

In alternative embodiments, compositions of the invention comprise a hydrogel comprising: 3-(tris(trimethylsiloxy)silyl)propyl methacrylate, tris(trimethylsiloxy) silylpropyl methacryloxyethyl carbamate, N-tris (trimethylsiloxysilylpropyl)acrylamide, and 1,3-bis (methacrylamidopropyl)1,1,3,3,-tetrakis(trimethylsiloxy) disiloxane-, methacryloxyalkylsiloxanes, 3-methacryloxy propylpentamethyldisiloxane, bis(methacryloxypropyl)tetramethyldisiloxane, monomethacrylated polydimethylsiloxane and/or monoacrylated polydimethylsiloxane and/or a mixture thereof.

For example, in alternative embodiments, compositions of the invention comprise a hydrogel prepared by crosslinking a hydrophilic biopolymer or a synthetic polymer, e.g., hydrogels formed from physical or chemical crosslinking of hydrophilic biopolymers such as hyaluronans, chitosans, alginates, collagen, dextran, pectin, carrageenan, polylysine, gelatin and/or agarose.

For example, in alternative embodiments, compositions of the invention comprise a hydrogel comprising: the water-swellable clay mineral hydrogels as described in U.S. Pat. No. 7,993,892; poly-N-isopropylacrylamide ("PNIPAM")-co-allylamine microgels, e.g., as described in U.S. Pat. No. 7,989,505; a superporous hydrogel, e.g., a hydrogel comprising an ethylenically-unsaturated monomer of hydroxyethyl methacrylate (HEMA), at least one cross-linking agent, and at least one property-modifying agent comprising an ion-complexable site, as described e.g., in U.S. Pat. No. 7,988,992; a-methacrylamidophenylboronic acid hydrogel, e.g., as described e.g., in U.S. Pat. No. 7,988,685; a hydrogel comprising a guanosine hydrazide derivative, a cation and a water-based liquid, e.g., as described e.g., in U.S. Pat. No. 7,981,436; a mesoporous hydrogel, e.g., as described e.g., in U.S. Pat. No. 7,968,085; a hydrolytically degradable hydrogel comprising crosslinked poly(ethylene)glycol (PEG) structures, e.g., as described e.g., in U.S. Pat. No. 7,964,217; a polyurethane hydrogel, e.g., as described e.g., in U.S. Pat. No. 7,947,863; a silicone hydrogel material, e.g., comprising a styrene monomer or a substituted styrene monomer, e.g., as described e.g., in U.S. Pat. No. 7,939,579; a p-vinylphenylboronic acid (VPBA) or a poly(N-alkyl acrylamide) or a poly(N-isopropylacrylamide) (NIPAm), e.g., as described e.g., in U.S. Pat. No. 7,935,518; a cationic hydrogel such as poly(N,N-ethylaminoethylmethacrylate) or poly(ethylene-alt-maleic anhydride), or a polyethylene glycol (PEG)-hydrogel copolymer, e.g., as described e.g., in U.S. Pat. No. 7,935,518; a nanocomposite hydrogel comprising a hydrophilic polymer such as a hydrophilic vinyl monomer, an acrylic acid, an acrylamide (AM) and a vinylpyrrolidone, an N-isopropylacrylamide (NIPAM) or an N-vinylformamide (NVF), crosslinked by a crosslinker comprising nanocrystalline cellulose (NCC), e.g., as described e.g., in U.S. patent application publication no. 20110182990; or a biodegradable starch-based hydrogel, e.g., as described e.g., in U.S. patent application publication no. 20100331232.

Hydrogels used to practice the invention, and/or compositions of the invention, can also comprise a diluent, such as a lactose monohydrate, calcium carbonate, calcium sulfate, microcrystalline cellulose, calcium phosphate, dextrin, dextrose, maltitol, maltose, starch, sucrose and/or talc and/or mixtures thereof Hydrogels used to practice the invention, and/or compositions of the invention, can also comprise a lubricating or an anti-sticking agent, e.g., a colloidal silica dioxide, talc, glyceryl monostearates, calcium stearate, magnesium stearate, magnesium silicate, glyceryl monostearates, stearic acid, glyceryl behenate, and/or polyethylene glycol.

Hydrogels used to practice the invention, and/or compositions of the invention, can also comprise a plasticizer, e.g., an acetyltributyl citrate, triacetin, acetylated monoglyceride, rape oil, olive oil, sesame oil, coconut oil, poloxamer, acetyltriethyl citrate, glycerin, sorbitol, diethyloxalate, diethylmalate, diethylfumerate, dibutylsuccinate, diethylmalonate, dioctylphthalate, dibutylphthalate, dibutylsebacate, triethyl citrate, tributylcitrate, glyceroltributyrate, polyethylene glycol and/or propylene glycol and/or mixtures thereof.

Magnetic Molecules or Particles

In alternative embodiments, compositions of the invention comprise a plurality of magnetic molecules or particles. Any magnetic molecules or particles can be used.

For example, in alternative embodiments, magnetic molecules or particles used to practice the invention comprise: dextran iron oxide nanoparticles; magnetically-responsive microparticles or nanoparticles as described, e.g., in U.S. Pat. No. 7,989,065, or magnetic microspheres, nanospheres, microbeads or nanobeads, as described, e.g., in U.S. Pat. No. 7,994,592; a superparamagnetic bead or polystyrene beads, as described, e.g., in U.S. Pat. No. 7,989,614, e.g., DYNABEADS™, Dynal AS (Oslo, Norway); or, superparamagnetic fine particles, as described, e.g., in U.S. Pat. Nos. 7,981,512; 7,713,627, or 7,399,523, describing spinel ferrimagnetic particles. In one embodiment, superparamagnetic particles comprising iron oxide having e.g., between about 0.1 to 10% by weight iron oxide based on the weight of the magnetic particles are used, e.g., as described in U.S. Pat. No. 5,368,933.

Any device that can separate a magnetic particle or molecule from a sample can be used, e.g., as a magnetic separator as described in U.S. Pat. Nos. 7,985,340; 6,143,577; or 5,770,461.

Enteric Capsules or Coatings

In alternative embodiments, compositions of the invention are encapsulated in an enteric coating, or encapsulated in a capsule, tablet or geltab or the like that partially or completely dissolves or disintegrates in duodenal pH, or at a pH of between about 5 and 6, or at a pH more alkaline than a pH of about 5. In alternative embodiments, these are formulated as tablets, geltabs or capsules and the like for oral administration.

Any enteric coating agents (partially or completely dissolves or disintegrates in duodenal pH) can be used, e.g., cellulose acetate phthalate, hydroxypropylmethylcellulose phthalate, hydroxypropylmethylcellulose acetate succinate, carboxymethylethylcellulose, methacrylic acid-methyl methacrylate copolymer and methacrylic acid-methyl acrylate copolymer, and natural products such as shellac, and mixtures thereof, e.g., as described in U.S. Pat. No. 4,670,287.

In alternative embodiments, tablets, geltabs or capsules (or any composition of the invention encapsulated by an enteric coating agent) further comprises an additional agent, for example, a protein or peptide, a polysaccharide, a fat, a lipid, a secretin, a DNase inhibitor, an EGTA, an EDTA, an actin, a polycation or a mixture thereof or a combination thereof.

The invention will be further described with reference to the examples described herein; however, it is to be understood that the invention is not limited to such examples.

EXAMPLES

Example 1

Exemplary Ingestible Nucleic Acid Capturing Compositions of the Invention and Methods for Making and Using them This example describes exemplary compositions of the invention, including exemplary ingestible nucleic acid-capturing devices, pills, beads, capsules, products of manufacture, particles, microparticles or nanoparticles of the invention. We've shown that in vitro exemplary hydrogel coated cationic compositions of the invention (e.g., a device, pill, bead, capsule, product of manufacture, particle or nanoparticle) can capture and protect a nucleic acid, e.g., a DNA, in presence of 20 mg/ml bile salts and 2 mg/ml pancreatic DNase II.

In alternative embodiments, the invention provides ingestible, cationic polymer-coated devices, capsules, products of manufacture, particles, microparticle or nanoparticles that can "capture" (or retain) and protect gastrointestinal, e.g., duodenal, nucleic acids, e.g., cancer DNA or RNA, in vivo. Confirming efficacy can be by using known amounts of tumor cells, which are fed to normal mice via an esophageal tube, followed by administration of exemplary compositions of the invention, e.g., optimized exemplary magnetic particle-comprising devices, capsules, products of manufacture, particles, microparticle or nanoparticles of the invention. The stool can be collected, particles recovered by a magnet, and nucleic acid can be isolated or detected and analyzed, e.g., the KRAS G12D mutation recovery can be quantified, e.g., by a PCR, e.g., a qPCR. The amount of particles necessary to improve the recovery can be optimized. Particles are fed to mice with a genetic pancreatic cancer (KPC), and the improvement in the sensitivity of detection of KRAS mutation in stool is tested by a statistical analysis.

Feasibility of DNA sampling with exemplary ingestible magnetic particles of the invention: nucleic acids, being polyphosphates, are negatively charged within a wide range of pH. Absorption of DNA to positively charged surfaces or molecules (e.g., the plurality of magnetic particles within or on a composition of the invention) is an extremely favorable thermodynamic process. The negative charge of DNA has been exploited in gene therapy, where cationic polymers and liposomes have been used for complexation of DNA and subsequent cellular delivery. These complexes exhibit increased stability of nucleic acids in the presence of serum DNases. While the invention is not limited by any particular mechanism of action, the protective effect can be explained by a limited access of DNases to the condensed nucleic acid, and to the neutralization of DNA charges, which makes it difficult for DNases to interact with the substrate.

In alternative embodiments, the ingestible compositions of the invention are formulated in the same or similar manner as the nano- and microparticles used for oral drug and gene delivery, e.g., in animal models (32, 34), or as radiological contrast agents in humans (35).

The nanoparticle and microparticle passage times in the gastrointestinal tract have been studied. Once ingested, particles of micron size rapidly (e.g., less than 30 min on an empty stomach (36)) transition into the duodenum, where they encounter high concentrations of bile acids, proteases and DNases. The cationic particles of composition of the invention will bind and protect nucleic acids and proteins or peptides in the gut, e.g., genomic DNA or RNA, in the presence of negatively charged bile acids and DNase I. Compositions of the invention with the attached nucleic acid, e.g., DNA or RNA, and/or protein or peptide will travel along to the intestine and colon.

In alternative embodiments, the nucleic acid- or protein-binding capacity of a composition of the invention already is saturated in the duodenum-ileum region; therefore nucleic acid, e.g., DNA or RNA, or proteins or peptides, from the colon epithelium and bacterial flora will absorb less. Most of the particle dose should be excreted within 24 hours (h) (about 95% of the dose), albeit not as a single fraction (37). Small particles (0.3 μm) are endocytosed by intestines to some extent (38). Once excreted in feces, the composition of the invention (now comprising, or coated with, nucleic acid, e.g., DNA or protein or peptide, e.g., via the plurality of cationic or anionic molecules contained in and/or on the composition) can be easily retrieved using e.g., color coding, an endoscope, a magnetic column, and the like. The nucleic acid, e.g., DNA or RNA, or proteins or peptides, can be recovered for subsequent analysis.

Example 2

Exemplary Nano- and Microparticles that Capture and Protect Cancer DNA in a Duodenal Environment In Vitro This example describes exemplary compositions of the invention, including exemplary nano- and microparticles that capture and protect cancer DNA in a duodenal Environment in vitro.

Design of DNA-Capturing Particles

Figure 3:
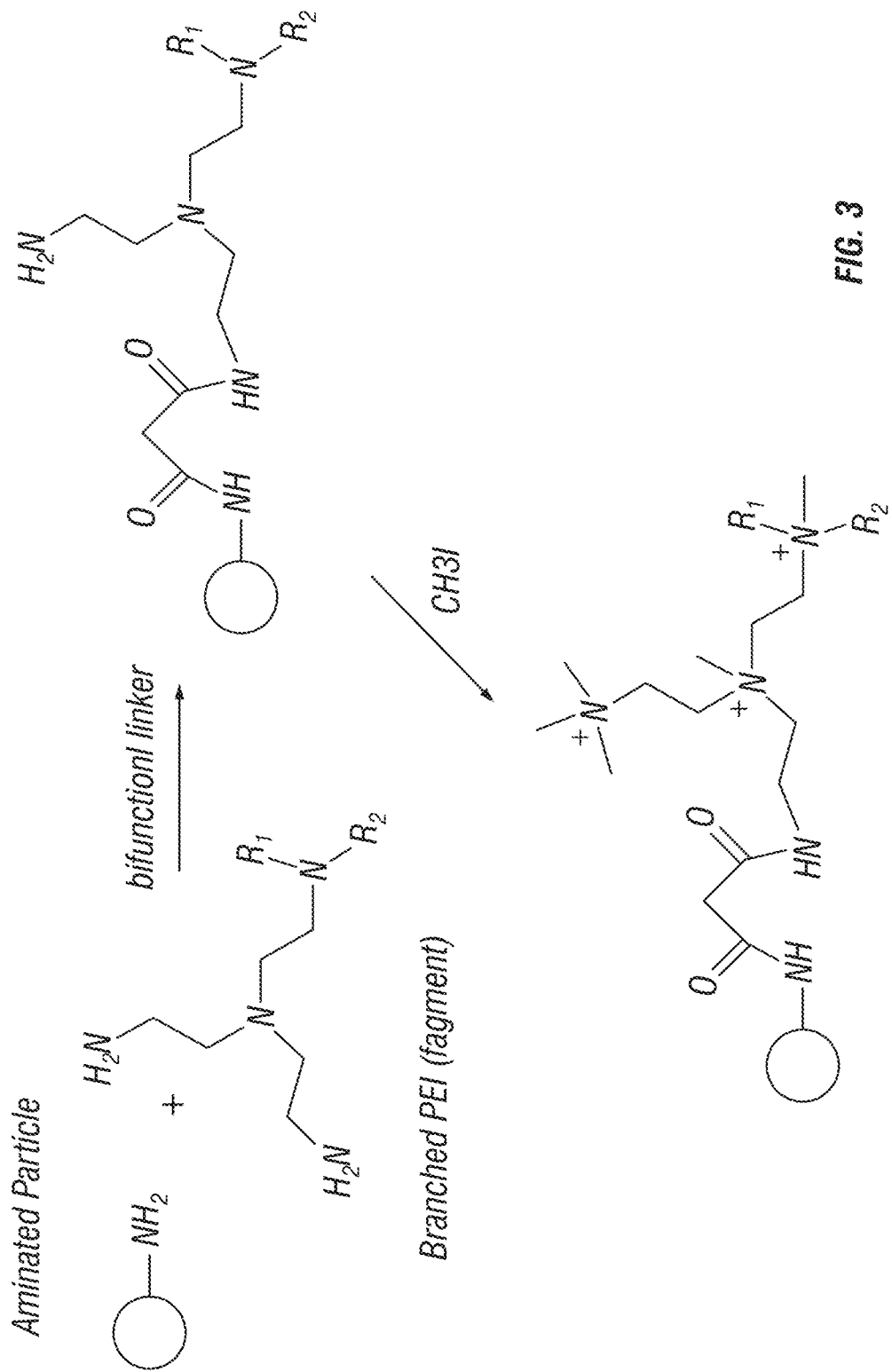
FIG. 3 illustrates an exemplary protocol, or synthesis scheme, of molecules or particles with a highly charged surface used in compositions of the invention, as described in Example 2, below.

FIG. 3 illustrates an exemplary protocol, or synthesis scheme, of molecules or particles with a highly charged surface used in compositions of the invention.

In alternative embodiments, nanoparticles and microparticles are based on an iron oxide $Fe_3O_4$ scaffold. This allows easy separation of the particles from solution or from stool using magnetic column. In alternative embodiments, the formulation or synthesis DNA-binding and magnetic nanoparticles is described e.g., in references: (39-43).

In alternative embodiments, as a precursor, 10 μm to 20 μm magnetic nanoparticles, which are available commercially are used. Alternatively, dextran-coated magnetic 100 nm to 300 nm nanoparticles are prepared by precipitation, e.g., as described in: (39). In alternative embodiments, dextran iron oxide nanoparticles approved in clinic for MRI contrast is used, e.g., as described in: (44). By changing the ratio of the amount of dextran to the amount of metal salts, the nanoparticles of different size and shape can be prepared, e.g., as described in: (45, 46).

Synthesis of aminated hydrogel-coated nanoparticles can be by any protocol; e.g., crosslinked dextran nanoparticles can be prepared by reacting 1-chloro-2,3-epoxypropane (epichlorohydrin) with dextran-coated SPIO in basic conditions, resulting in a crosslinked hydrogel coat; these can be aminated, e.g., as described in (39); see also FIG. 3. The advantage of larger particles is that they have higher chances of passing through the GI tract without being reabsorbed in the intestines or colon.

In alternative embodiments, in order to make particles that efficiently bind DNA in a wide range of pH, the surface are further modified, e.g., as illustrated in FIG. 3. Branched crosslinked dextran (e.g., of between about 10-500 kDa) or polyethylenimine (e.g., of between about 10-500 kDa) can be used for this purpose. In alternative embodiments, these polymers are attached to the particles through linker chemistry, and the primary and tertiary amines are quaternized using methyl iodide, see e.g. Scheme 1 in: (47). In alternative embodiments, strongly basic guanidinium groups (e.g., pKa 12.5) are attached to the hydrogel-coated particles. In alternative embodiments, the goal is to create a densely charged porous hydrogel surface with the high capacity for nucleic acid, e.g., DNA binding.

In alternative embodiments, dynamic light scattering, light and electron microscopy are used to characterize the size and shape of the particles. In alternative embodiments charge is characterized by e.g., a ZETA-SIZER™ (Malvern Instruments Ltd., Spectris, Surrey, England). Modification and amination of the particle surface will be characterized with Fourier transform infrared spectroscopy (FTIR, or FT-IR).

Binding of Purified Cancer DNA in the Presence of Bile Acids and DNase

Compositions of the invention are efficient binds of purified genomic DNA in presence of bile and DNase. In demonstrating this: genomic DNA from pancreatic cancer cells LMP-KRAS with KRAS mutation G12D (3) is extracted with phenol/chloroform and probe sonicated to generate fragments of 100-500 kDa. DNA is mixed with particles at different +/− ratios, in the presence of various concentrations (50-100 mg/ml) of bile acids and DNase (1-10 mg/ml). Bile acids form polyanionic micelles and theoretically can compete with the DNA for the particle surface binding, while DNase can degrade the DNA. Particles are washed, DNA eluted (see Preliminary data) and analyzed on agarose gel. DNA recovery efficiency is calculated.

Recovery of Cancer DNA Released from the Cells.

To demonstrate or confirm the recovery of mutant cancer DNA released from cells, the following is performed: various numbers of intact LMP-KRAS cells (3) will be added to a mixture of 1-10 mg/ml pancreatic DNase, 1-10 mg/ml trypsin and 10-100 mg/ml bile salts, followed by the cationic magnetic particles. Following the incubation at 37° C. for 30-180 min, the particles are washed (external magnet for microparticles or Miltenyi Biotec (Auburn, Calif.) MIDI column for nanoparticles), DNA is eluted (see Preliminary Data section), and analyzed for KRAS mutation. In alternative embodiments, allele-specific oligonucleotide PCRs (ASO-PCRs) are used, they can achieve a reported sensitivity better than 0.01% (48). In alternative embodiments, digital PCR technology incorporating nanofluidic devices or microdroplet reactors is used; these can further improve the sensitivity of detection (49-51).

In alternative embodiments, a protocol based on ASO-PCR is uses; commercial kits from TrimGen Corp. (Sparks, Md.) diagnostics and QIAGEN (Valencia, Calif.) also can be used. These kits are capable of detecting up to 7 different mutations in the KRAS codon 12, with sensitivity of 1% of mutant DNA in the sample. In alternative embodiments, the number of KRAS copies is quantified, and the DNA recovery efficiency is calculated.

Using agarose gel, greater than about 95% of the DNA can be recovered after addition of bile acids. This binding efficiency has been shown for highly charged polyethylenimine (52). According to our Preliminary Data, bile acids do not displace the DNA from the beads. The recovery of mutated DNA in the presence of bile salts and DNase depends on several parameters, such as release of the genomic DNA from cells and DNA protection on the particles' surface. Partial DNA fragmentation is not expected to prevent the PCR reaction, since this one is restricted to a short KRAS locus of approximately 150 base pairs (4) or even shorter.

Regarding recovery efficiency of DNA released from the cells, based on our preliminary data, we estimate the recovery to be between about 10% to 20%. Based on the recovery, is can be determined whether nanoparticles and microparticles are more efficient for any particular embodiment.

In vitro experiments might not accurately predict an in vivo behavior of any particular particle of the invention. For example, an important factor in vivo is the presence of actin (53) (a DNase inhibitor) in the pancreatic juice. EGTA is another efficient inhibitor that depletes Ca++, thus inactivating DNase and making it susceptible to trypsin digestion. If the recovery of KRAS mutated DNA is less than 1%, test for the presence of EGTA in the range of concentrations (2-100 mM) for improving the recovery.

Verifying Protection of Cancer DNA In Vivo by Compositions of the Invention

Testing and optimizing DNA protection in vivo can be done by administering exemplary particles of the invention and cancer DNA to normal mice, for example, by feeding a known amount of cancer cells to mice and quantifying the recovery. Larger animal models also can be used.

In human studies, sensitivity of KRAS mutation detection in stool using conventional extraction methods was about 50% (25). In alternative embodiments, this sensitivity of detection can be achieved using exemplary particles of the invention. One exemplary verifying protocol comprises: C57/BL6 mice are intubated through their esophagus. Intact pancreatic cancer cells LMP-KRAS with KRAS mutation G12D (3) are administered. First, greater than about $10^6$ cells to 10 mice are administered. The stool is collected over 6-10 hours. The gastrointestinal passage times in mice is about 3 to 6 hours (54), after which almost 80% of the ingested matter should be excreted (54). DNA is extracted using, in addition to, or as a control alternative to, compositions of the invention, a QIAAMP™ (QIAamp™) stool DNA extraction kit. KRAS mutation is quantified by PCR; e.g., TttTt-KRAS is quantified by PCR.

To calculate the sensitivity, a "yes" or "no" for the presence of a KRAS mutation in stool is determined. The number of cells needed in order to achieve the detection in stool in 50% of mice is determined Next, the same number of cells are administered to C57/BL6 mice followed by the magnetic particles (approximately 0.1 to 0.5 mg Fe). Stool is collected, and the particles are magnetically separated from the rest of the fecal mass. Particle-bound DNA and free DNA are isolated and quantified by qPCR. The sensitivity of PCR is at the level of single copies. The DNA recovery is calculated for particle-bound DNA, free DNA and total DNA (stool DNA/input DNA). The sensitivity of DNA detection is calculated (see statistics below). The particle recovery in stool is determined by QUANTICHROM™ (Gentaur, Kampenhout, Belgium) iron assay, as described e.g., in: (41), which has a sensitivity of 0.1 µg, or less than 0.1% of the administered dose. The recovery of DNA is normalized to the amount of the recovered iron.

Statistics: A logistic regression model is used to determine the number of cancer cells needed to achieve a KRAS mutation detection rate of 50%; e.g., about 10 mice can be used for this purpose. A one-sided Fisher's Exact test is used to compare the detection rate between particle treated mice and control mice; at a significance level of 5%, 36 mice per group is needed to have 80% power to detect a significant difference if the rates are 50% in the control group and ≥80% in the treated mice. To compare sensitivities using particle bound DNA vs. total stool DNA, a McNemar's test is used.

Compositions of the invention, including a device, pill, bead, capsule, product of manufacture, particle, microparticle or nanoparticle of the invention, is tested or calibrated e.g., by administering particles to pancreatic cancer mouse models, e.g., a tumor model that pathologically reproduces early pancreatic cancer lesions (PanINs) and recaptures the molecular signature of early pancreatic cancer. An LSL-KrasG12D/+; LSL-Trp53R172H/+; Pdx-1-Cre (KPC) mouse model, as described e.g., in: (55), can be used; this model has both KRAS and p53 mutations. The mice develop pancreatic tumors within 5 to 6 months (source can be: Dr. Lowy, Moores Cancer Center, UCSD, San Diego, Calif.).

The tumors become imageable when they reach about 3 to 4 mm in size. At this stage, the disease is local. Compositions of the invention (e.g., particles of the invention) are administered through esophageal tubing at the early stage; and when the tumor doubles in size it is assessed by palpitation and ultrasound. The stool is collected and analyzed for KRAS mutations as described above. Both particle-bound and particle-free fraction of DNA in stool is analyzed. As a positive control, KRAS mutations are determined in the tumor tissue.

Statistics: The statistical tests are performed to determine the benefit of using exemplary compositions of the invention (e.g., particles) for detection of the KRAS mutation in a stool sample. At each stage, 36 KPC mice per group are needed to assess whether administered particles increase the detection sensitivity of KRAS mutation in stool. A one-sided Fisher's exact test can be used to compare between groups, at a significance level of 5%. Here, we assume the sensitivities for control mice and particle treated mice are 20% vs. 50%, respectively, at early stage, 50% vs. 80% at late stage. Particle-bound and particle-free DNA in stool is summarized for the treated groups.

Exemplary compositions of the invention (e.g., particles) can improve the recovery of orally administered DNA in a stool. The recovery and the sensitivity of detection of KRAS in particle-administered mice should be statistically different from the control group (no particles). For pancreatic cancer bearing mice, a 30% increase in the sensitivity in the particle group is considered significant using the proposed number of mice. With more advanced tumors the sensitivity is increased in both particle treated and control group.

The sensitivity depends on multiple factors, including the number of cancer cells shed from the tumor, efficiency of genomic DNA release by bile acids, lipases and proteases, DNA destruction by DNases, capture by the beads, and survival of the captured DNA during the passage inside the GI tract.

Studies can be performed to optimize the interaction of a cancer DNA with compositions of the invention (e.g., particles) in vivo. Recovery of KRAS mutations after feeding mice with particles precoated with the cancer DNA can be determined and measured. If the recovery is low, this could mean that the DNA is degraded/dissociated during the GI tract passage. To optimize: the dose of compositions of the invention (e.g., particles) and/or charge density of the particles is increased (but below the toxic dose); oral administration of a DNase inhibitor (EGTA) also can be tested.

To promote tumor cell destruction in the GI tract, vegetable oil can be administered to stimulate bile secretion. If KRAS mutated DNA is not detectable in stool of KPC mice (either control or particle-treated), mice can be injected with intravenous (IV) mouse secretin (Genescript, Piscataway, N.J.). Secretin stimulates pancreas to produce and secrete pancreatic juice, and is used in patients prior to the endoscopic collection of pancreatic juice. Increased secretion from the pancreas can induce secretion of the cells.

Figure 4:
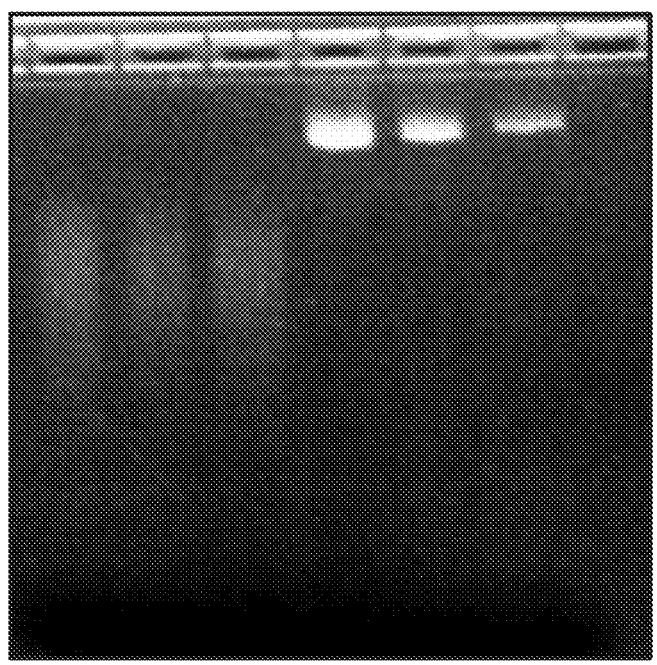
FIG. 4 illustrates a DNA analysis on an agarose gel, as described in Example 2, below.

FIG. 4 illustrates a DNA analysis on an agarose gel. Sonicated calf thymus DNA and plasmid DNA were used (left 3 bands and right 3 bands, respectively. Lanes 1,4: DNA only; Lanes 2,5: DNA was incubated with particles and eluted by salt; lanes 3,6: DNA was incubated with magnetic particles+30 mg/ml bile acids. Particles retain large proportion of DNA even in the presence of bile acids.

Magnetic particles (5-10 µm diameter) with primary amines were purchased from Polysciences Inc. (Warrington, Pa.). The particles were washed and activated with formaldehyde as described in the manufacturer's manual. Then, 1 mg of the beads were added to 10 mg/ml solution of polyethylenimine (10-15 kDa, branched) in 0.1M bicarbonate buffer (pH 8.0) and allowed to react for 5 h at room temperature with stirring. The particles were washed using external magnet for 3 times.

For studying interaction with DNA, sonicated calf thymus DNA was used. Five microgram of DNA was added to 20 µg beads suspension in PBS. In addition, the bile acids (Sigma, St. Louis, Mo.) at 10 mg/ml final solution were added. Following the incubation for 20 min, the particles were washed 5 times in PBS, and the DNA was eluted in a small volume of 1.5M NaCl. The DNA was dialyzed using a SLIDE-A-LYZER™ (Slide-A-Lyzer™) (Thermo Fisher Scientific, Rockford, Ill.) MINI (10 kDa cutoff) for 1 h to get rid of the salt, and the DNA was loaded on 2% agarose gel (EZ Gel, Invitrogen, LifeSciences, Carlsbad, Calif.) and analyzed (FIG. 3).

Figure 5:
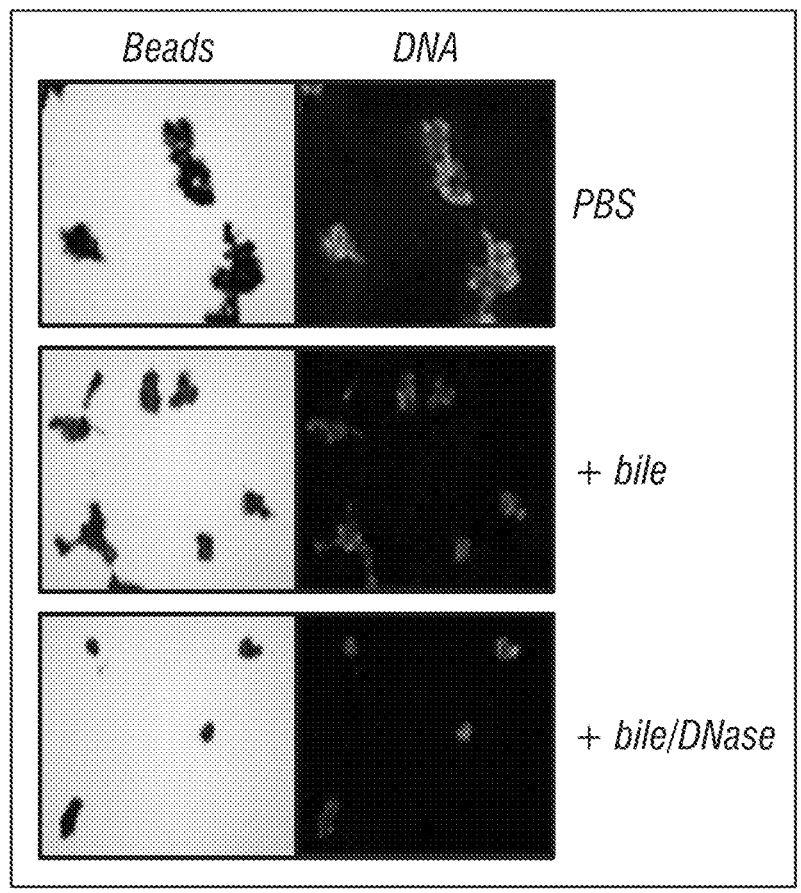
FIG. 5 and FIG. 6 illustrate the presence of DNA in (attached to or in) the beads following DNase and bile treatment; DNA was incubated with beads and various components of duodenal secretions.
Figure 6:
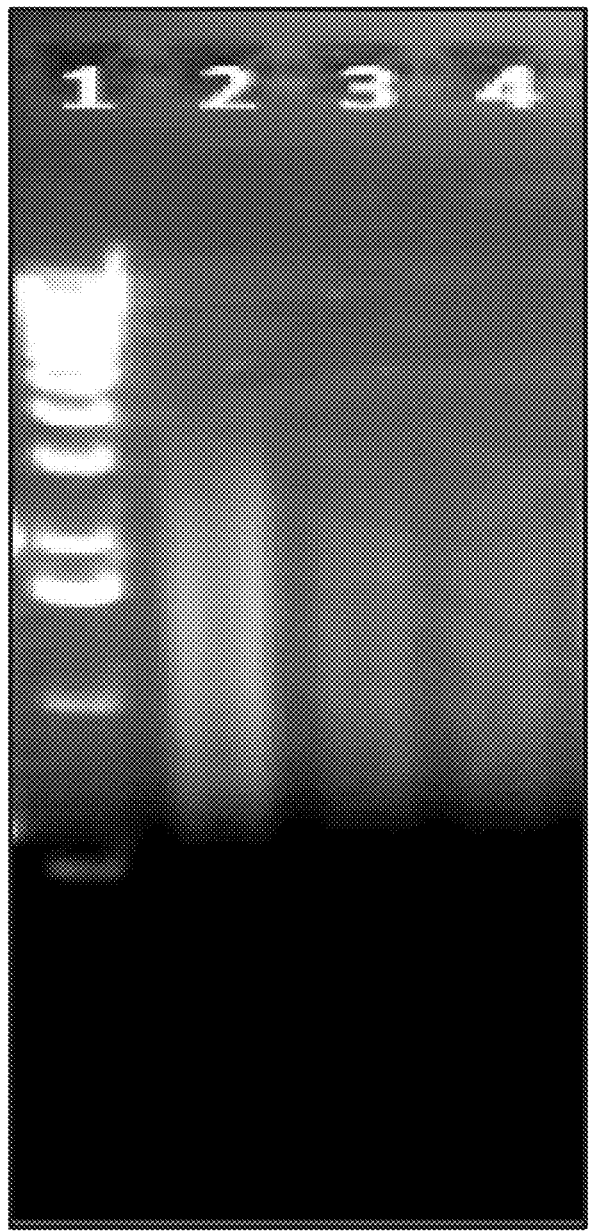
Figure 7:
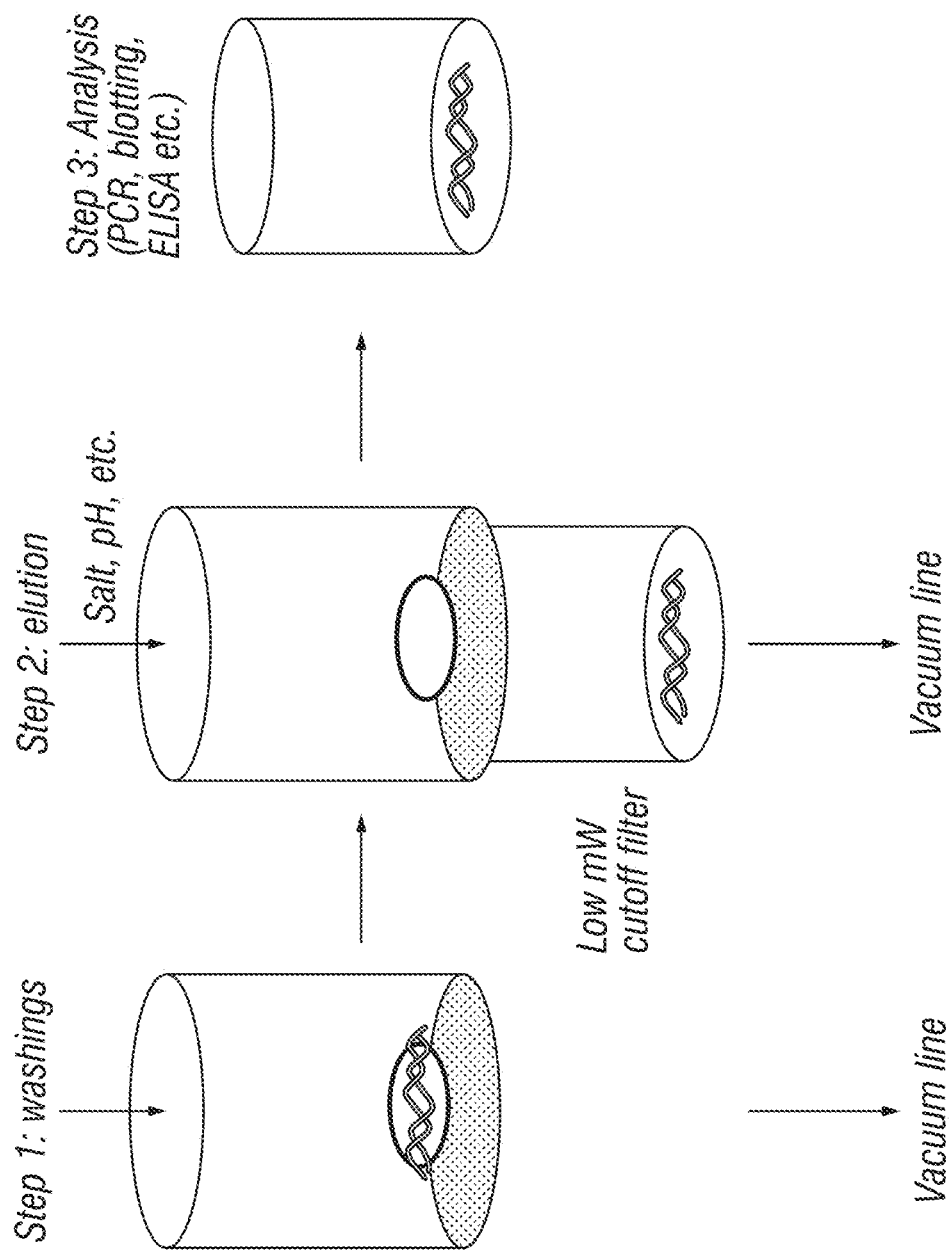
FIG. 7 illustrates an exemplary purification protocol of the invention using a device of the invention comprising: a vacuum wash, an elution and an entrapment of the eluted material in a lower compartment equipped with low cut off filter. The trapped analyte can be processed directly in a downstream analysis technique.

In another experiment, the particles were incubated with sonicated genomic DNA, bile salts and DNase I from porcine pancreas (Sigma, St. Louis, Mo.) at 1 mg/ml. A small aliquot of the beads after the washing steps but before DNA elution was stained with SYBR Gold (Invitrogen, LifeSciences, Carlsbad, Calif.) for microscopy analysis (FIG. 5). The eluted DNA was analyzed on the agarose gel. FIG. 5 and FIG. 6: illustrate the presence of DNA in (attached to or in) the beads following DNase and bile treatment. DNA was incubated with beads and various components of duodenal secretions. FIG. 5: illustrates images of DNA stained with SyBr Gold. Bile and DNase decreased the amount of absorbed DNA, but did not completely remove it. FIG. 6 illustrates DNA analyzed on agarose gel stained with CyBr Green. Lane 2, beads+DNA+PBS; lane 3, beads+DNA+bile acids; Lane 4, beads+DNA+DNAse+bile acids. According to the data, even the non-optimized aminated particles have a protective effect on calf thymus DNA in the presence of DNase and bile acids, although there was a decrease in the amount of DNA per particle and partial DNA degradation.

REFERENCES

1. Maitra A, Hruban R H. 2008. Pancreatic cancer. Annu Rev Pathol 3: 157-88
2. Ferrari Junior A P, Lichtenstein D R, Slivka A, Chang C, Carr-Locke D L. 1994. Brush cytology during ERCP for the diagnosis of biliary and pancreatic malignancies. Gastrointest Endosc 40: 140-5
3. Tseng W W, Winer D, Kenkel J A, Choi O, Shain A H, Pollack J R, French R, Lowy A M, Engleman E G. 2010. Development of an Orthotopic Model of Invasive Pancreatic Cancer in an Immunocompetent Murine Host. Clinical Cancer Research 16: 3684-95

4. Hingorani S R, Petricoin E F, Maitra A, Rajapakse V, King C, Jacobetz M A, Ross S, Conrads T P, Veenstra T D, Hitt B A, Kawaguchi Y, Johann D, Liotta L A, Crawford H C, Putt M E, Jacks T, Wright C V, Hruban R H, Lowy A M, Tuveson D A. 2003. Preinvasive and invasive ductal pancreatic cancer and its early detection in the mouse. Cancer Cell 4: 437-50
5. Rosty C, Goggins M. 2002. Early detection of pancreatic carcinoma. Hematol Oncol Clin North Am 16: 37-52
6. Teich N, Mossner J. 2004. Molecular analysis of pancreatic juice: a helpful tool to differentiate benign and malignant pancreatic tumors? Dig Dis 22: 235-8
7. Ahlquist D A. 2010. Molecular detection of colorectal neoplasia. Gastroenterology 138: 2127-39
8. Lynch H T, Deters C A, Snyder C L, Lynch J F, Villeneuve P, Silberstein J, Martin H, Narod S A, Brand R E. 2005. BRCA1 and pancreatic cancer: pedigree findings and their causal relationships. Cancer Genetics and Cytogenetics 158: 119-25
9. Everhart J, Wright D. 1995. Diabetes-Mellitus as a Risk Factor for Pancreatic-Cancer—a Metaanalysis. Jama-Journal of the American Medical Association 273: 1605-9
10. Michaud D S, Giovannucci E, Willett W C, Colditz G A, Stampfer M J, Fuchs C S. 2001. Physical activity, obesity, height, and the risk of pancreatic cancer. Jama-Journal of the American Medical Association 286: 921-9
11. Michaud D S, Liu S M, Giovannucci E, Willett W C, Colditz G A, Fuchs C S. 2002. Dietary sugar, glycemic load, and pancreatic cancer risk in a prospective study. Journal of the National Cancer Institute 94: 1293-300
12. Lowenfels A B, Maisonneuve P. 2006. Epidemiology and risk factors for pancreatic cancer. Best Practice & Research in Clinical Gastroenterology 20: 197-209
13. Klump B, Hsieh C J, Nehls O, Dette S, Holzmann K, Kiesslich R, Jung M, Sinn U, Ortner M, Porschen R, Gregor M. 2003. Methylation status of p14ARF and p16INK4a as detected in pancreatic secretions. Br J Cancer 88: 217-22
14. Matsubayashi H, Canto M, Sato N, Klein A, Abe T, Yamashita K, Yeo C J, Kalloo A, Hruban R, Goggins M. 2006. DNA methylation alterations in the pancreatic juice of patients with suspected pancreatic disease. Cancer Res 66: 1208-17
15. Cristofanilli M, Budd G T, Ellis M J, Stopeck A, Matera J, Miller M C, Reuben J M, Doyle G V, Allard W J, Terstappen L W, Hayes D F. 2004. Circulating tumor cells, disease progression, and survival in metastatic breast cancer. N Engl J Med 351: 781-91
16. Diehl F, Li M, Dressman D, He Y, Shen D, Szabo S, Diaz L A, Jr., Goodman S N, David K A, Juhl H, Kinzler K W, Vogelstein B. 2005. Detection and quantification of mutations in the plasma of patients with colorectal tumors. Proc Natl Acad Sci USA 102: 16368-73
17. Castells A, Puig P, Mora J, Boadas J, Boix L, Urgell E, Sole M, Capella G, Lluis F, Fernandez-Cruz L, Navarro S, Farre A. 1999. K-ras mutations in DNA extracted from the plasma of patients with pancreatic carcinoma: diagnostic utility and prognostic significance. J Clin Oncol 17: 578-84
18. Allard W J, Matera J, Miller M C, Repollet M, Connelly M C, Rao C, Tibbe A G, Uhr J W, Terstappen L W. 2004. Tumor cells circulate in the peripheral blood of all major carcinomas but not in healthy subjects or patients with nonmalignant diseases. Clin Cancer Res 10: 6897-904
19. Berthelemy P, Bouisson M, Escourrou J, Vaysse N, Rumeau J L, Pradayrol L. 1995. Identification of K-ras mutations in pancreatic juice in the early diagnosis of pancreatic cancer. Ann Intern Med 123: 188-91
20. Shi C, Fukushima N, Abe T, Bian Y, Hua L, Wendelburg B J, Yeo C J, Hruban R H, Goggins M G, Eshleman J R. 2008. Sensitive and quantitative detection of KRAS2 gene mutations in pancreatic duct juice differentiates patients with pancreatic cancer from chronic pancreatitis, potential for early detection. Cancer Biol Ther 7: 353-60
21. Tada M, Omata M, Kawai S, Saisho H, Ohto M, Saiki R K, Sninsky J J. 1993. Detection of ras gene mutations in pancreatic juice and peripheral blood of patients with pancreatic adenocarcinoma. Cancer Res 53: 2472-4
22. Yamada T, Nakamori S, Ohzato H, Oshima S, Aoki T, Higaki N, Sugimoto K, Akagi K, Fujiwara Y, Nishisho I, Sakon M, Gotoh M, Monden M. 1998. Detection of K-ras gene mutations in plasma DNA of patients with pancreatic adenocarcinoma: correlation with clinicopathological features. Clin Cancer Res 4: 1527-32
23. Ahlquist D A. 2009. Next-generation stool DNA testing: expanding the scope. Gastroenterology 136: 2068-73
24. Itzkowitz S H. 2009. Incremental advances in excremental cancer detection tests. J Natl Cancer Inst 101: 1225-7
25. Caldas C, Hahn S A, Hruban R H, Redston M S, Yeo C J, Kern S E. 1994. Detection of K-ras mutations in the stool of patients with pancreatic adenocarcinoma and pancreatic ductal hyperplasia. Cancer Res 54: 3568-73
26. Berndt C, Haubold K, Wenger F, Brux B, Muller J, Bendzko P, Hillebrand T, Kottgen E, Zanow J. 1998. K-ras mutations in stools and tissue samples from patients with malignant and nonmalignant pancreatic diseases. Clin Chem 44: 2103-7
27. Harries D, May S, Gelbart W M, Ben-Shaul A. 1998. Structure, stability, and thermodynamics of lamellar DNA-lipid complexes. Biophys J 75: 159-73
28. May S, Ben-Shaul A. 2004. Modeling of cationic lipid-DNA complexes. Curr Med Chem 11: 151-67
29. Feigner P L, Gadek T R, Holm M, Roman R, Chan H W, Wenz M, Northrop J P, Ringold G M, Danielsen M. 1987. Lipofection: a highly efficient, lipid-mediated DNA-transfection procedure. Proc Natl Acad Sci USA 84: 7413-7
30. Yi S W, Yune T Y, Kim T W, Chung H, Choi Y W, Kwon I C, Lee E B, Jeong S Y. 2000. A cationic lipid emulsion/DNA complex as a physically stable and serum-resistant gene delivery system. Pharm Res 17: 314-20
31. Moret I, Esteban Penis J, Guillem V M, Benet M, Revert F, Dasi F, Crespo A, Alino S F. 2001. Stability of PEI-DNA and DOTAP-DNA complexes: effect of alkaline pH, heparin and serum. J Control Release 76: 169-81
32. Dass C R, Choong P F M. 2008. Chitosan-mediated orally delivered nucleic acids: A gutful of gene therapy. Journal of Drug Targeting 16: 257-61
33. Martien R, Loretz B, Schnurch A B. 2006. Oral gene delivery: Design of polymeric carrier systems shielding toward intestinal enzymatic attack. Biopolymers 83: 327-36
34. Cheng J J, Teply B A, Jeong S Y, Yim C H, Ho D, Sherifi I, Jon S, Farokhzad O C, Khademhosseini A, Langer R S. 2006. Magnetically responsive polymeric microparticles for oral delivery of protein drugs. Pharmaceutical Research 23: 557-64
35. Lonnemark M, Hemmingsson A, Bachgansmo T, Ericsson A, Oksendal A, Nyman R, Moxnes A. 1989. Effect of Superparamagnetic Particles as Oral Contrast-Medium at Magnetic-Resonance Imaging—a Phase-I Clinical-Study. Acta Radiologica 30: 193-6

36. Camilleri M, Colemont L J, Phillips S F, Brown M L, Thomforde G M, Chapman N, Zinsmeister A R. 1989. Human gastric emptying and colonic filling of solids characterized by a new method. Am J Physiol 257: G284-90
37. Kreuter J, Muller U, Munz K. 1989. Quantitative and Micro autoradiographic Study on Mouse Intestinal Distribution of Polycyanoacrylate Nanoparticles. International Journal of Pharmaceutics 55: 39-45
38. Jenkins P G, Howard K A, Blackhall N W, Thomas N W, Davis S S, Ohagan D T. 1994. Microparticulate Absorption from the Rat Intestine. Journal of Controlled Release 29: 339-50
39. Park J H, von Maltzahn G, Zhang L, Derfus A M, Simberg D, Harris T J, Ruoslahti E, Bhatia S N, Sailor M J. 2009. Systematic surface engineering of magnetic nanoworms for in vivo tumor targeting. Small 5: 694-700
40. Simberg D, Zhang W M, Merkulov S, McCrae K, Park J H, Sailor M J, Ruoslahti E. 2009. Contact activation of kallikrein-kinin system by superparamagnetic iron oxide nanoparticles in vitro and in vivo. J Control Release 140: 301-5
41. Simberg D, Park J H, Karmali P P, Zhang W M, Merkulov S, McCrae K, Bhatia S N, Sailor M, Ruoslahti E. 2009. Differential proteomics analysis of the surface heterogeneity of dextran iron oxide nanoparticles and the implications for their in vivo clearance. Biomaterials 30: 3926-33
42. Simberg D, Weisman S, Talmon Y, Barenholz Y. 2004. DOTAP (and other cationic lipids): Chemistry, biophysics, and transfection. Critical Reviews in Therapeutic Drug Carrier Systems 21: 257-317
43. Simberg D, Weiss A, Barenholz Y. 2005. Reversible mode of binding of serum proteins to DOTAP/cholesterol lipoplexes: A possible explanation for intravenous lipofection efficiency. Human Gene Therapy 16: 1087-96
44. Bulte J W, Kraitchman D L. 2004. Iron oxide M R contrast agents for molecular and cellular imaging. NMR Biomed 17: 484-99
45. Gupta A K, Gupta M. 2005. Synthesis and surface engineering of iron oxide nanoparticles for biomedical applications. Biomaterials 26: 3995-4021
46. Laurent S, Forge D, Port M, Roch A, Robic C, Vander Elst L, Muller R N. 2008. Magnetic iron oxide nanoparticles: synthesis, stabilization, vectorization, physicochemical characterizations, and biological applications. Chem Rev 108: 2064-110
47. Palermo E F, Kuroda K. 2009. Chemical structure of cationic groups in amphiphilic polymethacrylates modulates the antimicrobial and hemolytic activities. Biomacromolecules 10: 1416-28
48. Willis S G, Lange T, Demehri S, Otto S, Crossman L, Niederwieser D, Stoffregen E P, McWeeney S, Kovacs I, Park B, Druker B J, Deininger M W. 2005. High-sensitivity detection of BCR-ABL kinase domain mutations in imatinib-naive patients; correlation with clonal cytogenetic evolution but not response to therapy. Blood 106: 2128-37
49. Oehler V G, Qin J, Ramakrishnan R, Facer G, Ananthnarayan S, Cummings C, Deininger M, Shah N, McCormick F, Willis S, Daridon A, Unger M, Radich J P. 2009. Absolute quantitative detection of ABL tyrosine kinase domain point mutations in chronic myeloid leukemia using a novel nanofluidic platform and mutation-specific PCR. Leukemia 23: 396-9
50. Li M, Diehl F, Dressman D, Vogelstein B, Kinzler K W. 2006. BEAMing up for detection and quantification of rare sequence variants. Nature Methods 3: 95-7
51. Shi C J, Eshleman S H, Jones D, Fukushima N, Hua L, Parker A R, Yeo C J, Hruban R H, Goggins M G, Eshleman J R. 2004. LigAmp for sensitive detection of single-nucleotide differences. Nature Methods 1: 141-7
52. Brissault B, Kichler A, Guis C, Leborgne C, Danos O, Cheradame H. 2003. Synthesis of linear polyethylenimine derivatives for DNA transfection. Bioconjug Chem 14: 581-7
53. Funakoshi A, Wakasugi H, Nakamura M, Takagi Y, Ibayashi H. 1980. Biochemical and clinical studies on human pancreatic deoxyribonuclease I inhibitor. Gastroenterol Jpn 15: 592-9
54. Dawson N J. 1972. Rate of passage of a non-absorbable marker through the gastrointestinal tract of the mouse (*Mus musculus*). Comp Biochem Physiol A Comp Physiol 41: 877-81
55. Hingorani S R, Wang L F, Multani A S, Combs C, Deramaudt T B, Hruban R H, Rustgi A K, Chang S, Tuveson D A. 2005. Trp53(R172H) and KraS(G12D) cooperate to promote chromosomal instability and widely metastatic pancreatic ductal adenocarcinoma in mice. Cancer Cell 7: 469-83

Example 3

Exemplary Compositions of the Invention

This example describes exemplary compositions of the invention, and describes their effectiveness in harvesting nucleic acids. This study used sonicated thymus DNA to test the stability in the presence of cationic polymers bile and DNase.

Quaternized polyethylenimine (PEI) was prepared from branched PEI (Sigma, St. Louis, Mo.) using methyl iodide in potassium carbonate/chloroform. After reacting under reflux overnight, the mixture was filtered and chloroform and $CH_3I$ were evaporated.

Polymer was dissolved in PBS/5 mM calcium (Ca), mixed with sonicated calf thymus DNA, followed by pancreatic Dnase I (1 mg/ml), bile (30 mg/ml) and trypsin (1-5 mg/ml), separately or together. The control polymers included protamine sulfate and branched PEI.

Figure 8:
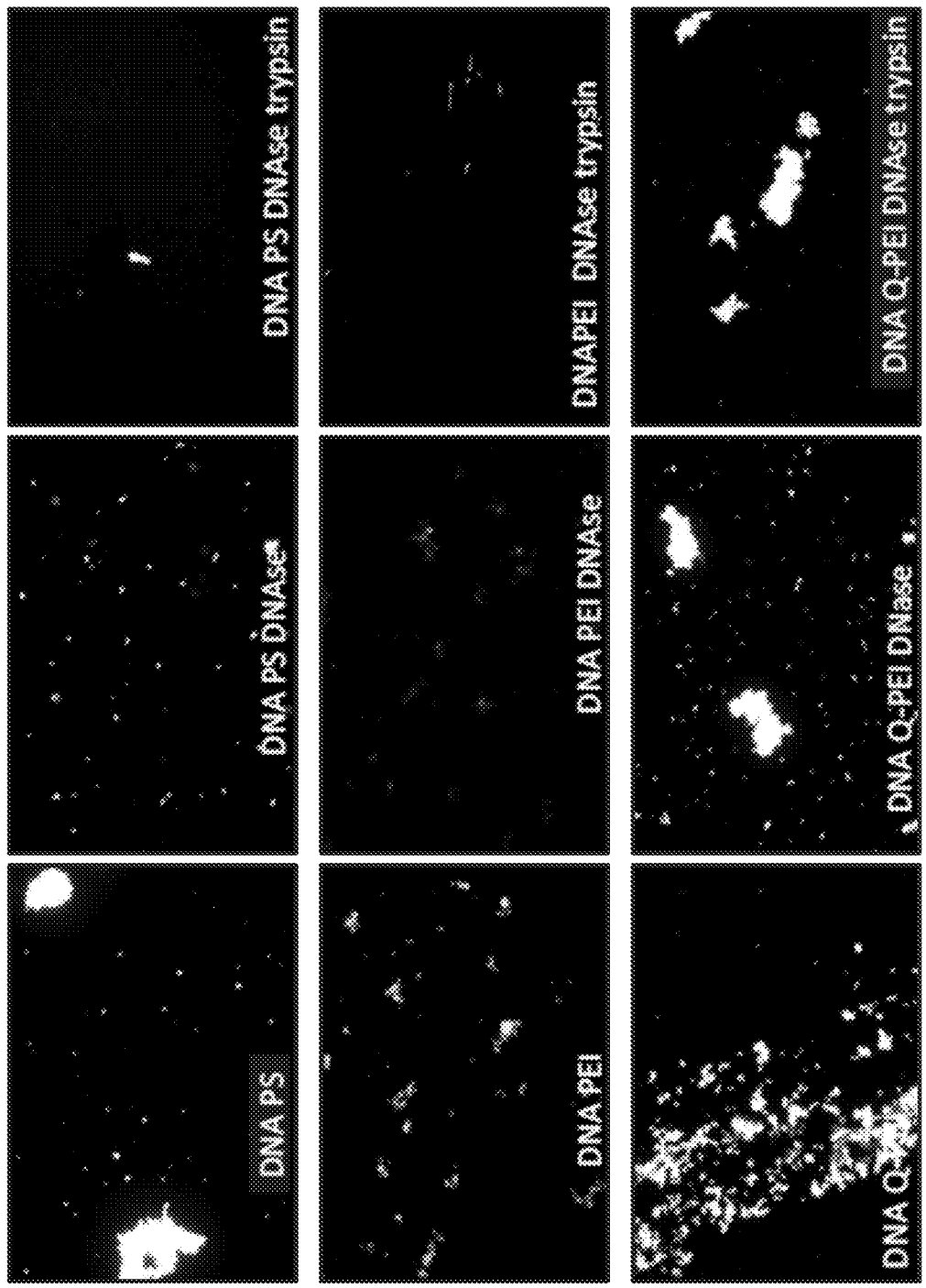
FIG. 8 illustrates fluorescence images of sonicated thymus DNA tested in the presence of cationic polymers bile and DNase, as described in Example 3, below.

The mixture was incubated at 37° C. for 1 hour (h), SyBr Gold was added and the remaining DNA was visualized under microscope by fluorescence, as illustrated in FIG. 8. FIG. 8 describes the polymers tested as: protamine sulfate (PS); poly-L-lysine; PEI; PEI with quaternary amines (Q).

Composition of the pancreatic juice: DNase 1 mg/ml; $Ca^{++}$ 5 mM; bile 20 mg/ml trypsin 1 mg/ml. These were incubated at 37 C for 1 hour (h).

As illustrated in the FIG. 8 fluorescence images: all polymers showed DNA binding. Stability was determined by SyBr green fluorescence. PEI quaternary and PEI showed about 20% DNA stability. PLL and Protamine showed no remaining DNA.

A number of embodiments of the invention have been described. Nevertheless, it will be understood that various modifications may be made without departing from the spirit and scope of the invention. Accordingly, other embodiments are within the scope of the following claims.

What is claimed is:

1. A layered particle for retrieving DNA released from cells from a human gastrointestinal sample comprising:
   an outer shell or layer and an inner core or layer,
   wherein the outer shell or layer comprises an outer surface that is hydrophilic, and is neutral in charge, and the outer shell or layer comprises pores having a pore size of between 1 nm and 100 nm;
   and the inner core or layer comprises positively charged cationic polymers or molecules attached onto its outer surface, wherein the positively charged cationic polymers or molecules comprise
   a positively charged branched, cross-linked dextran or a quaternized positively charged branched, cross-linked polyethylenimine, or a combination thereof.

2. The layered particle of claim 1, wherein the inner core or layer further comprises a quaternary, a tertiary, a primary or a secondary amine, or a combination thereof, or a guanidine, a quaternized polyethylenimine (PEI), a pentamethylguanidine, a heptamethylisobiguanide or a Hunig's base or a mixture thereof.

3. The layered particle of claim 1, wherein the outer shell or layer and/or an inner core or layer further comprises a plurality of magnetic molecules or particles.

4. The layered particle of claim 1,
   wherein the positively charged cationic inner core or layer comprises a nanoparticle, microparticle or polymer that is positively charged (cationic).

5. The layered particle of claim 1, formulated for ingestion for a human.

6. A gel, a capsule, a tablet, a liquid, a spray, an emulsion, a suspension, a paste, a yogurt, or a geltab, comprising: a layered particle of claim 1.

7. The layered particle of claim 1, wherein the pores have a pore size of 1.5 nm.

8. The layered particle of claim 5, wherein the layered particle is encapsulated in:
   (a) an enteric coating, wherein optionally the enteric coating comprises a coating resistant in the gastric pH but removable in human duodenal pH, or dissolves or disintegrates in human duodenal pH; or
   (b) a capsule, tablet or geltab that dissolves or disintegrates in human duodenal pH, or at a pH of between pH 5 and pH 6.

9. The layered particle of claim 3, wherein the plurality of magnetic molecules or particles comprise a magnetically-responsive microparticle or nanoparticle; a superparamagnetic bead or polystyrene bead; a superparamagnetic fine particle; a ferrimagnetic particle; a magnetic microsphere; a magnetic microbead; or, a magnetic nanobead.

10. The gel, capsule, tablet, liquid, spray, emulsion, suspension, paste, yogurt, or geltab of claim 6, further comprising a DNase inhibitor, an EGTA, an EDTA, an actin, a polycations, a flavoring agent or a coloring agent, or a mixture thereof or a combination thereof.

11. The layered particle of claim 1, wherein the pores have a pore size of 2 nm, 2.5 nm, 3 nm, 3.5 nm or 4 nm.

12. The layered particle of claim 11, wherein the pores have a pore size of 5 nm, 10 nm or 15 nm.

13. The layered particle of claim 12, wherein the pores have a pore size of 20 nm, 25 nm, 30 nm or 40 nm.

14. The layered particle of claim 13, wherein the pores have a pore size of 50 nm, 60 nm, 70 nm, 80 nm, or 90 nm.

15. The layered particle of claim 1, wherein the positively-charged branched, cross-linked dextran or the positively-charged branched, cross-linked quaternized polyethylenimine (PEI) comprises positively-charged branched, cross-linked dextran or positively-charged branched, cross-linked quaternized polyethylenimine (PEI) of between 10 to 500 kDa.

16. The layered particle of claim 1, wherein the inner core or layer has attached onto its outer surface molecules comprising a positively charged branched, cross-linked dextran.

17. The layered particle of claim 1, wherein the inner core or layer has attached onto its outer surface molecules comprising a positively charged branched, cross-linked quaternized polyethylenimine (PEI).

18. The layered particle of claim 2, wherein the inner core or layer further comprises a quaternary, a tertiary, a primary or a secondary amine, or a combination thereof.

19. The layered particle of claim 2, wherein the inner core or layer further comprises a guanidine, a quaternized polyethylenimine (PEI), a pentamethylguanidine, a heptamethylisobiguanide or a Hunig's base or a mixture thereof.

* * * * *